United States Patent
Sepetka et al.

(10) Patent No.: US 8,267,940 B2
(45) Date of Patent: *Sep. 18, 2012

(54) SYSTEMS, METHODS AND DEVICES FOR REMOVING OBSTRUCTIONS FROM A BLOOD VESSEL

(75) Inventors: Ivan Sepetka, Los Altos, CA (US); Son Gia, San Jose, CA (US); John Miller, Redwood City, CA (US); Ryan Pierce, Mountain View, CA (US); Maria Aboytes, Palo Alto, CA (US); Tiffany Tran Ngo, San Jose, CA (US)

(73) Assignee: Concentric Medical, Inc., Mountain View, CA (US)

( * ) Notice: Subject to any disclaimer, the term of this patent is extended or adjusted under 35 U.S.C. 154(b) by 1656 days.

This patent is subject to a terminal disclaimer.

(21) Appl. No.: 10/973,888

(22) Filed: Oct. 25, 2004

(65) Prior Publication Data

US 2005/0059995 A1 Mar. 17, 2005

Related U.S. Application Data

(63) Continuation of application No. 10/839,977, filed on May 5, 2004, now Pat. No. 7,766,921, which is a continuation-in-part of application No. 10/460,751, filed on Jun. 11, 2003, now abandoned, which is a continuation-in-part of application No. 10/055,714, filed on Jan. 22, 2002, now Pat. No. 7,285,126, which is a continuation-in-part of application No. 09/891,141, filed on Jun. 25, 2001, now Pat. No. 6,824,545, which is a continuation-in-part of application No. 09/756,476, filed on Jan. 8, 2001, now Pat. No. 6,663,650, which is a continuation-in-part of application No. 09/605,143, filed on Jun. 29, 2000, now Pat. No. 6,730,104.

(51) Int. Cl.
*A61B 17/24* (2006.01)
*A61M 29/00* (2006.01)

(52) U.S. Cl. .......................... 606/113; 606/114; 606/200

(58) Field of Classification Search .................. 606/113, 606/114, 127, 200, 110, 159
See application file for complete search history.

(56) References Cited

U.S. PATENT DOCUMENTS

| | | | |
|---|---|---|---|
| 3,868,956 A | 3/1975 | Alfidi et al. |
| 3,996,938 A | 12/1976 | Clark, III |
| 4,655,771 A | 4/1987 | Wallsten |
| 4,706,671 A | 11/1987 | Weinrib |
| 4,807,626 A | 2/1989 | McGirr |
| 4,873,978 A | 10/1989 | Ginsburg |
| 4,890,611 A | 1/1990 | Monfort et al. |
| 4,969,891 A | 11/1990 | Gewertz |
| 4,994,069 A | 2/1991 | Ritchart et al. |
| 4,998,539 A | 3/1991 | Delsanti |

(Continued)

FOREIGN PATENT DOCUMENTS

AU 758524 3/2003

(Continued)

*Primary Examiner* — Corrine M McDermott
*Assistant Examiner* — Melissa Ryckman
(74) *Attorney, Agent, or Firm* — Jens Hoekendijk

(57) ABSTRACT

Devices and methods for removing an obstruction from a blood vessel are described. The devices are deployed in a collapsed condition and are then expanded within the body. The devices are then manipulated to engage and remove the obstruction.

5 Claims, 24 Drawing Sheets

U.S. PATENT DOCUMENTS

| | | | |
|---|---|---|---|
| 5,011,488 | A | 4/1991 | Ginsburg |
| 5,054,501 | A | 10/1991 | Chuttani et al. |
| 5,071,407 | A | 12/1991 | Termin et al. |
| 5,256,146 | A | 10/1993 | Ensminger et al. |
| 5,514,176 | A | 5/1996 | Bosley, Jr. |
| 5,527,326 | A | 6/1996 | Hermann et al. |
| 5,549,626 | A | 8/1996 | Miller et al. |
| 5,562,698 | A | 10/1996 | Parker |
| 5,688,234 | A | 11/1997 | Frisbie |
| 5,702,413 | A | 12/1997 | Lafontaine |
| 5,814,064 | A * | 9/1998 | Daniel et al. ............... 606/200 |
| 5,817,104 | A | 10/1998 | Bilitz et al. |
| 5,895,398 | A | 4/1999 | Wensel et al. |
| 6,066,149 | A * | 5/2000 | Samson et al. ............... 606/159 |
| 6,066,158 | A * | 5/2000 | Engelson et al. ............ 606/200 |
| 6,179,859 | B1 | 1/2001 | Bates et al. |
| 6,245,089 | B1 | 6/2001 | Daniel et al. |
| 6,375,668 | B1 | 4/2002 | Gifford et al. |
| 6,425,909 | B1 | 7/2002 | Dieck et al. |
| 6,436,112 | B2 | 8/2002 | Wensel et al. |
| 6,485,497 | B2 | 11/2002 | Wensel et al. |
| 6,494,884 | B2 | 12/2002 | Sepetka et al. |
| 6,530,935 | B2 | 3/2003 | Wensel et al. |
| 6,636,758 | B2 | 10/2003 | Sanchez et al. |
| 6,638,245 | B2 | 10/2003 | Miller et al. |
| 6,663,650 | B2 * | 12/2003 | Sepetka et al. ............... 606/200 |
| 6,692,508 | B2 | 2/2004 | Wensel et al. |
| 6,692,509 | B2 | 2/2004 | Wensel et al. |
| 6,702,782 | B2 | 3/2004 | Miller et al. |
| 6,730,104 | B1 | 5/2004 | Sepetka et al. |
| 6,746,468 | B1 | 6/2004 | Sepetka et al. |
| 6,824,545 | B2 * | 11/2004 | Sepetka et al. ............... 606/113 |
| 6,890,341 | B2 | 5/2005 | Dieck et al. |
| 6,905,503 | B2 | 6/2005 | Gifford et al. |
| 6,953,465 | B2 | 10/2005 | Dieck et al. |
| 7,058,456 | B2 | 6/2006 | Pierce |
| 7,285,126 | B2 * | 10/2007 | Sepetka et al. ............... 606/200 |
| 7,534,252 | B2 | 5/2009 | Sepetka et al. |
| 7,691,122 | B2 | 4/2010 | Dieck et al. |
| 7,727,242 | B2 | 6/2010 | Sepetka et al. |
| 7,727,243 | B2 | 6/2010 | Sepetka et al. |
| 7,766,049 | B2 | 8/2010 | Miller et al. |
| 7,766,921 | B2 | 8/2010 | Sepetka et al. |
| 8,062,307 | B2 | 11/2011 | Sepetka et al. |
| 8,105,333 | B2 | 1/2012 | Sepetka et al. |
| 2005/0033348 | A1 * | 2/2005 | Sepetka et al. ............... 606/200 |
| 2005/0085849 | A1 * | 4/2005 | Sepetka et al. ............... 606/200 |
| 2008/0183198 | A1 * | 7/2008 | Sepetka et al. ............... 606/159 |

FOREIGN PATENT DOCUMENTS

| | | |
|---|---|---|
| AU | 773570 | 9/2004 |
| AU | 2003204826 | 11/2006 |
| JP | S60-189973 | 8/1985 |
| JP | 02-077245 | 3/1990 |
| JP | 5-179916 | 5/1995 |

* cited by examiner

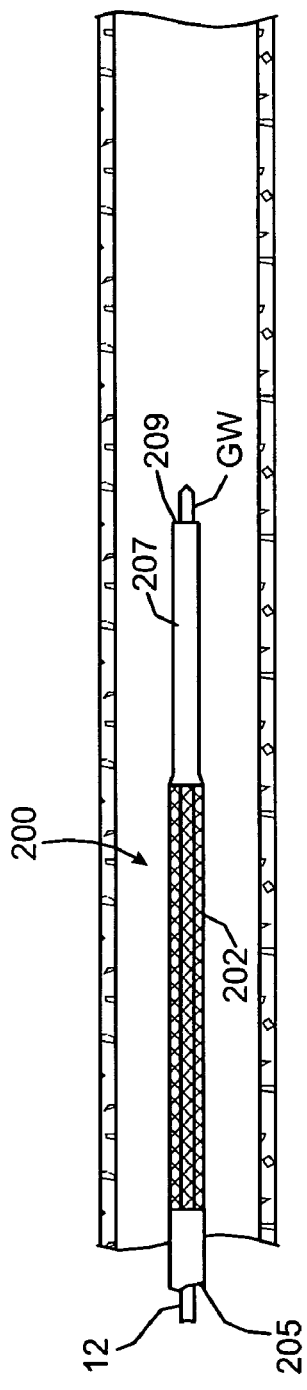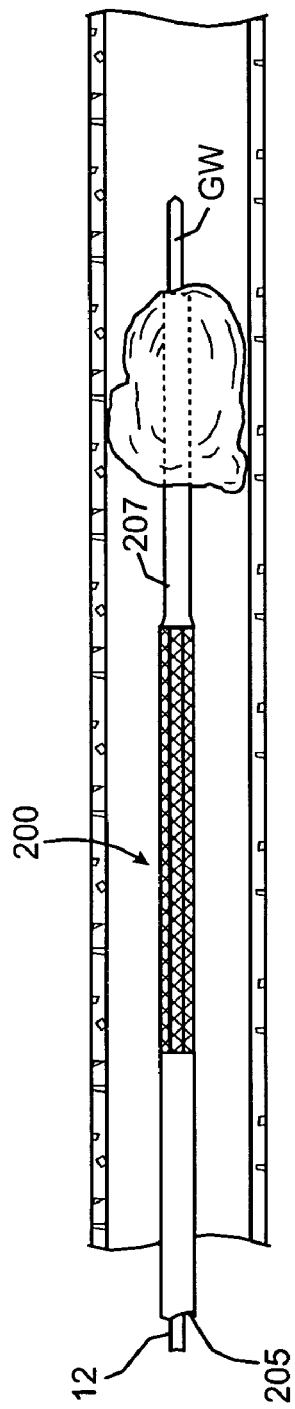
FIG. 7
FIG. 8

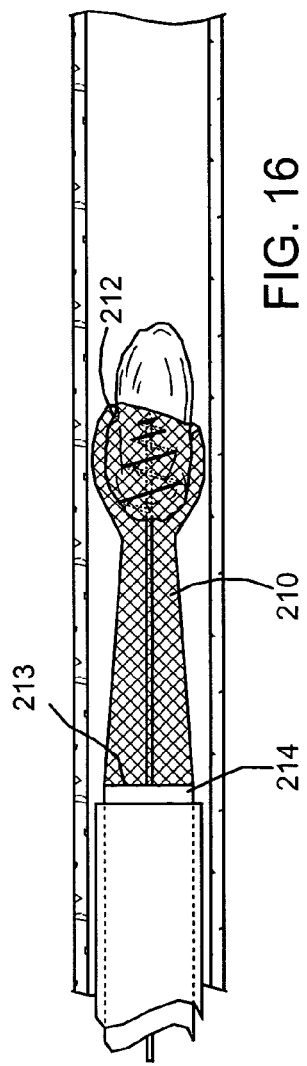
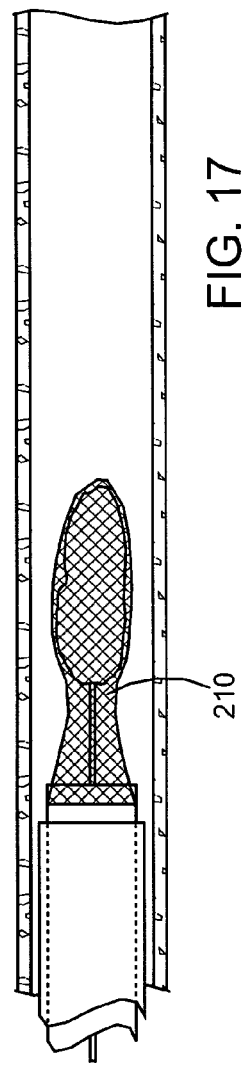
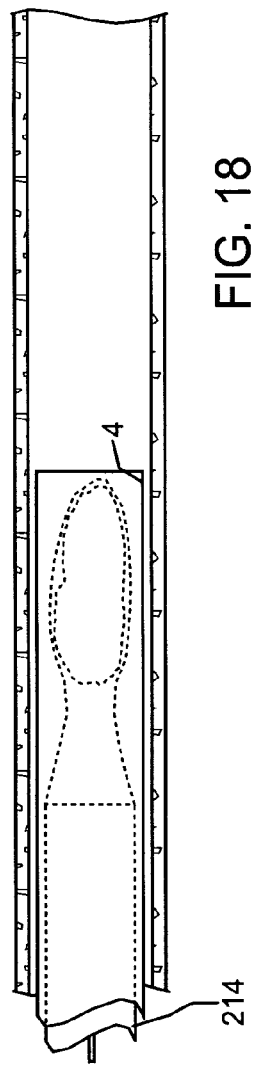

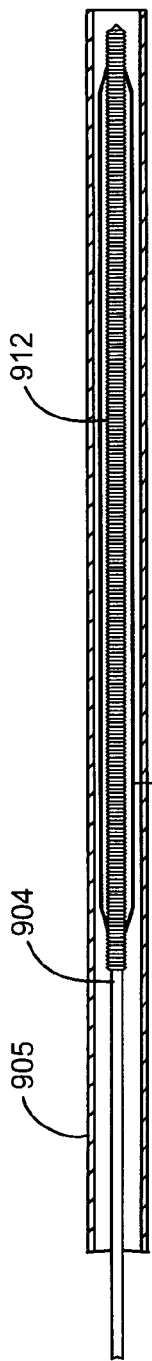
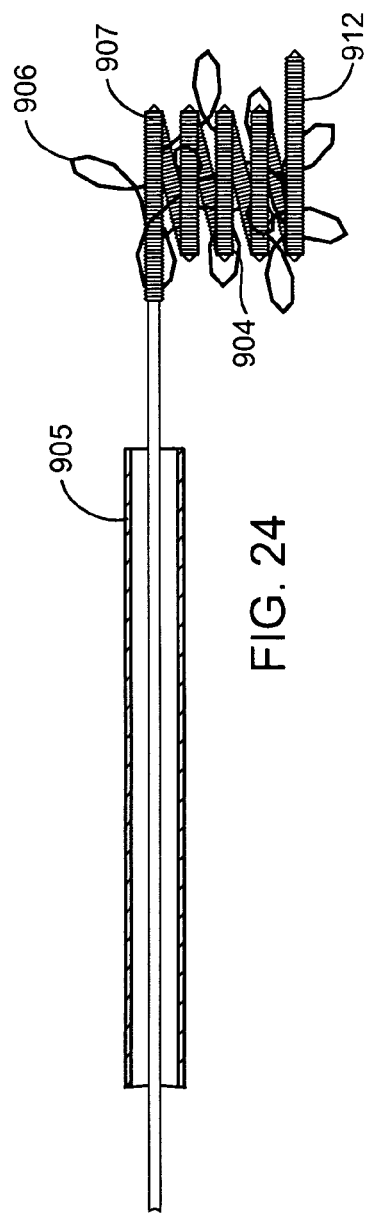
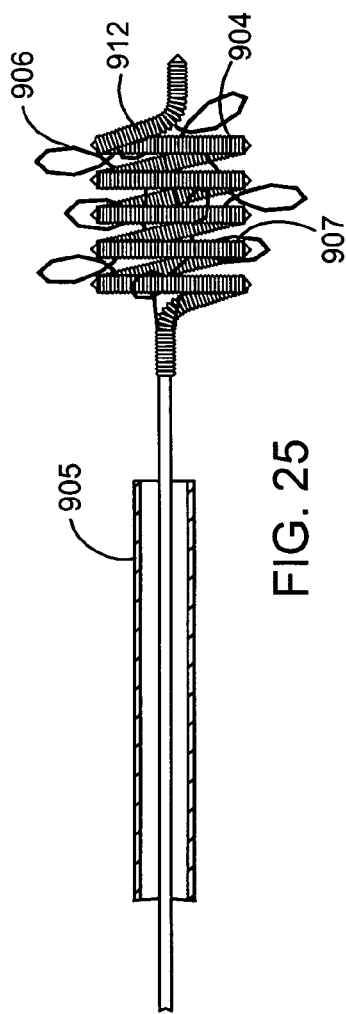
FIG. 23
FIG. 24
FIG. 25

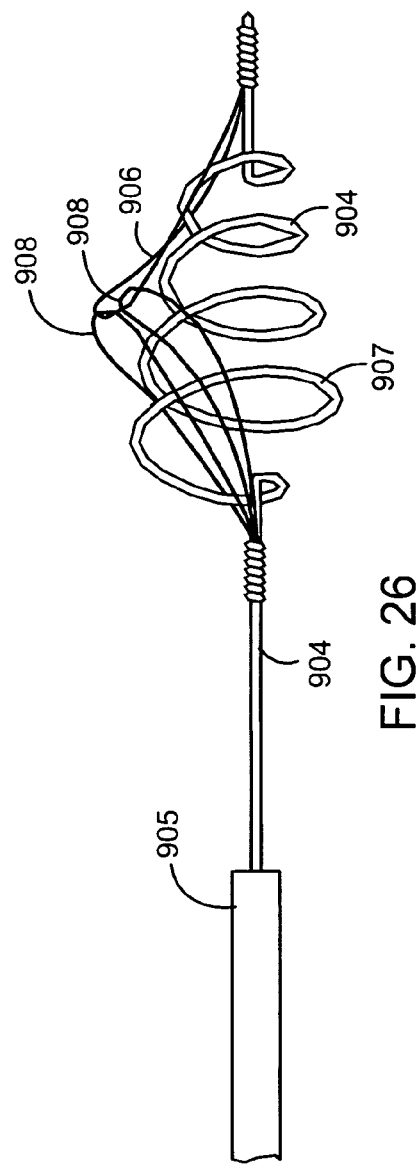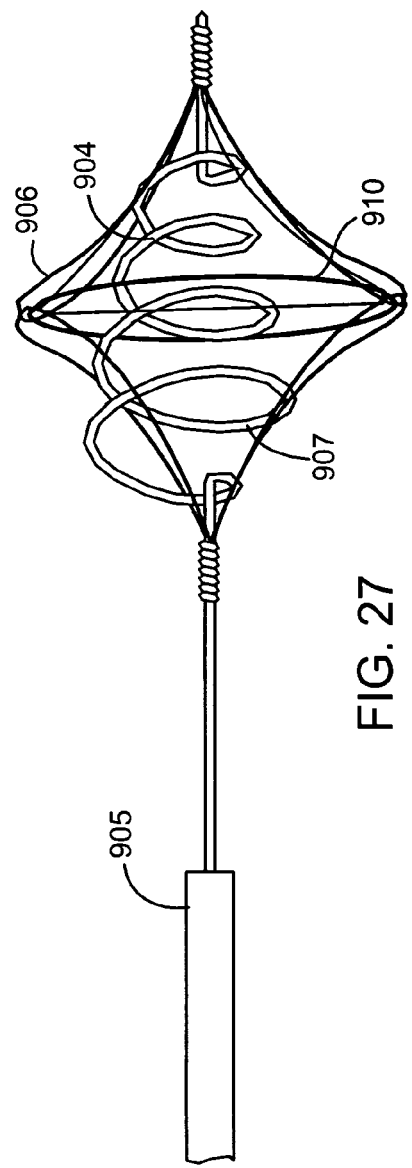

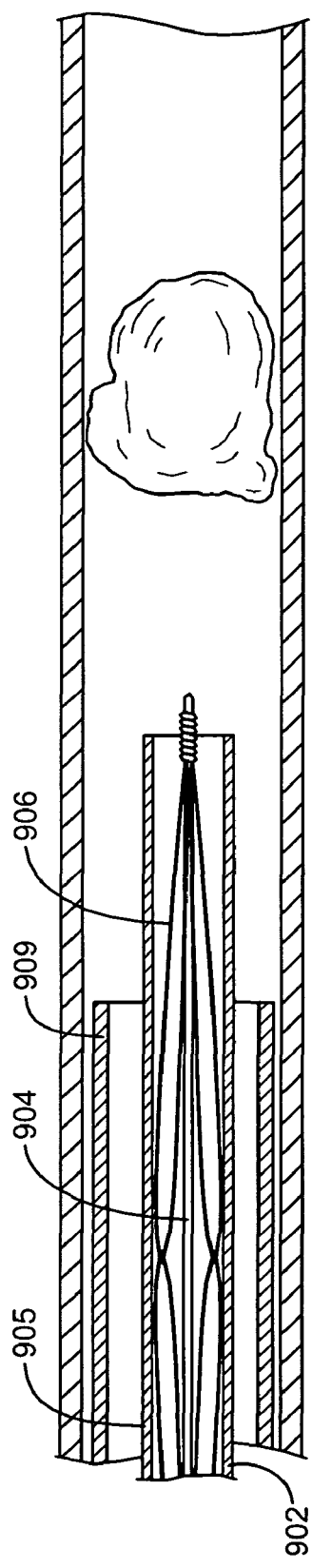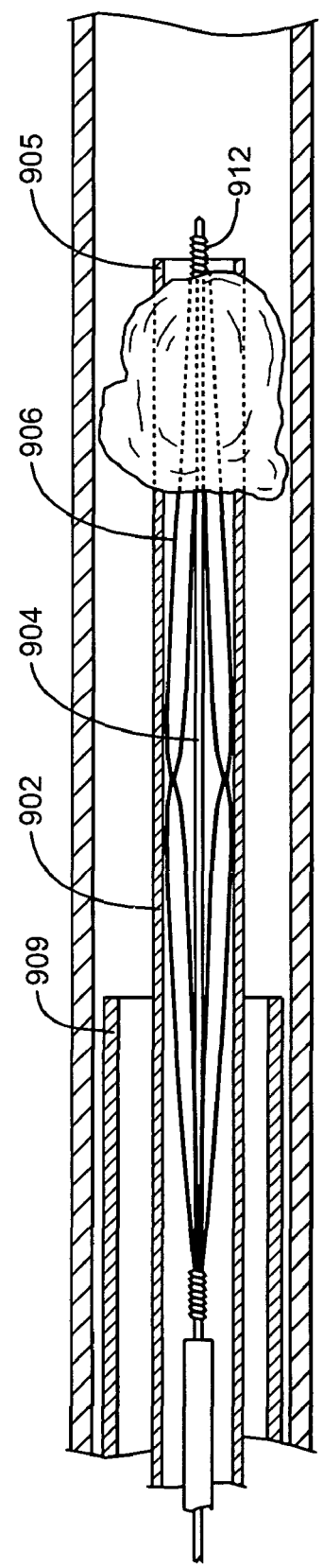

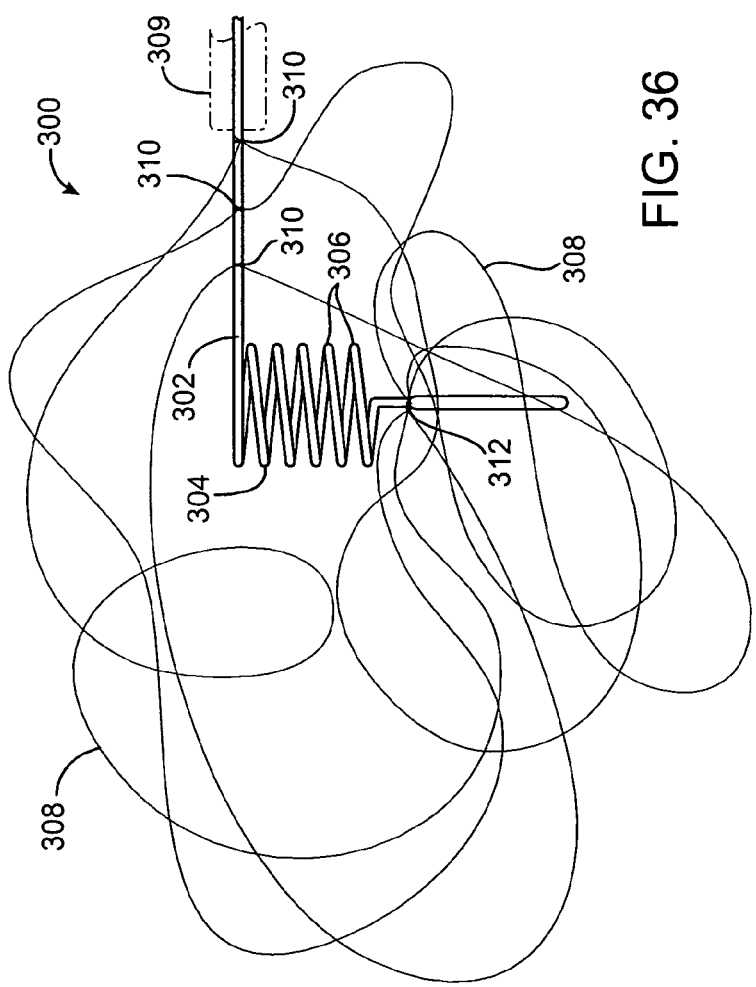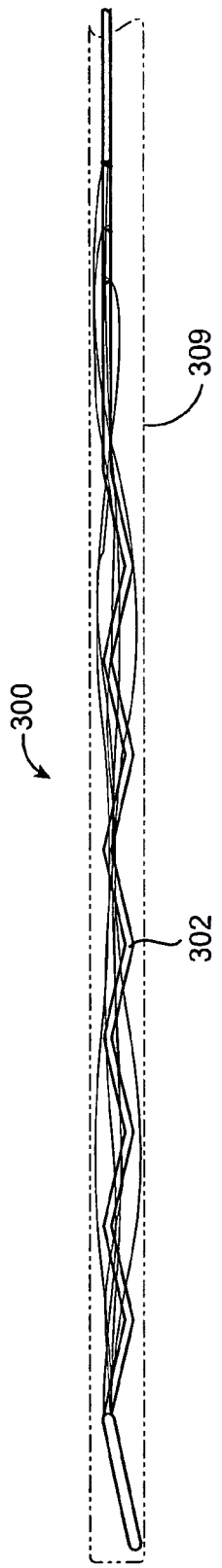

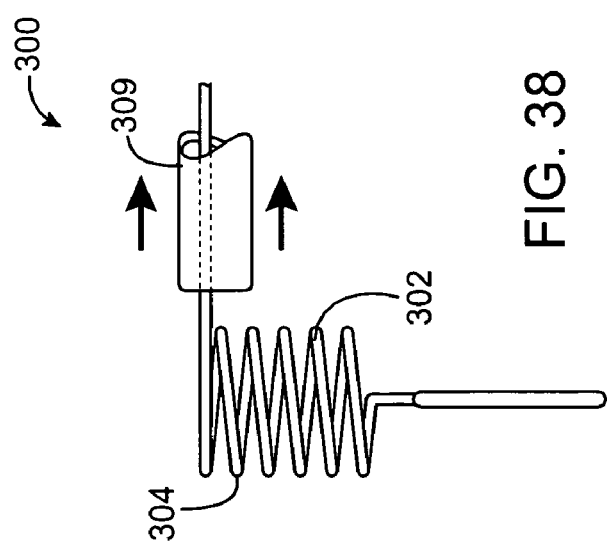
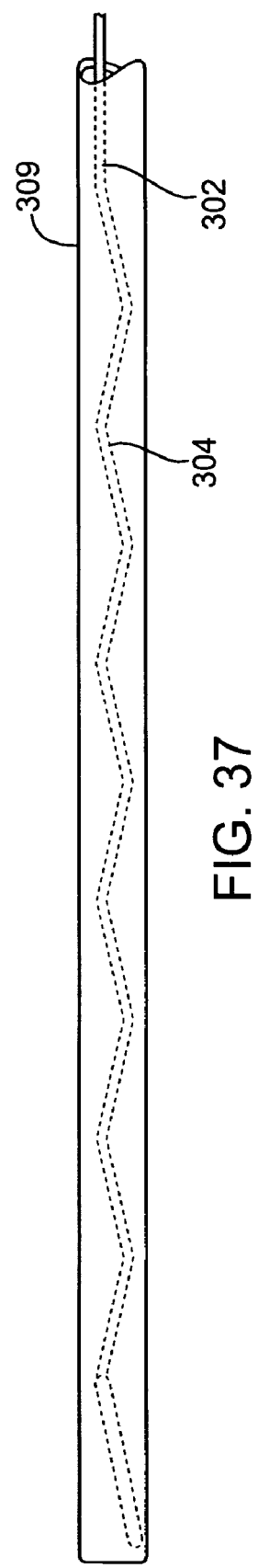
FIG. 38
FIG. 37

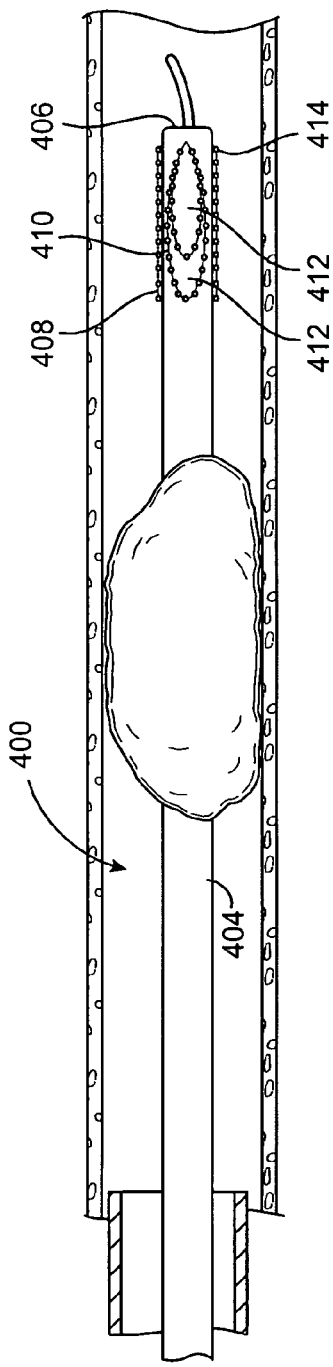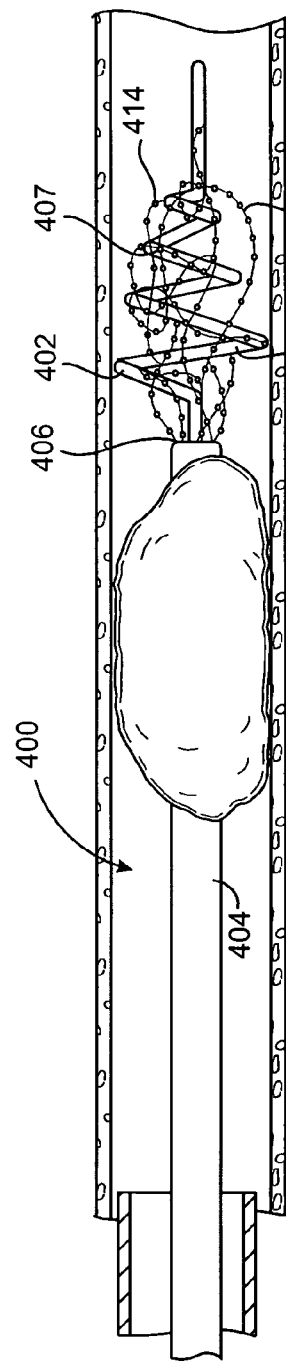
FIG. 39
FIG. 40

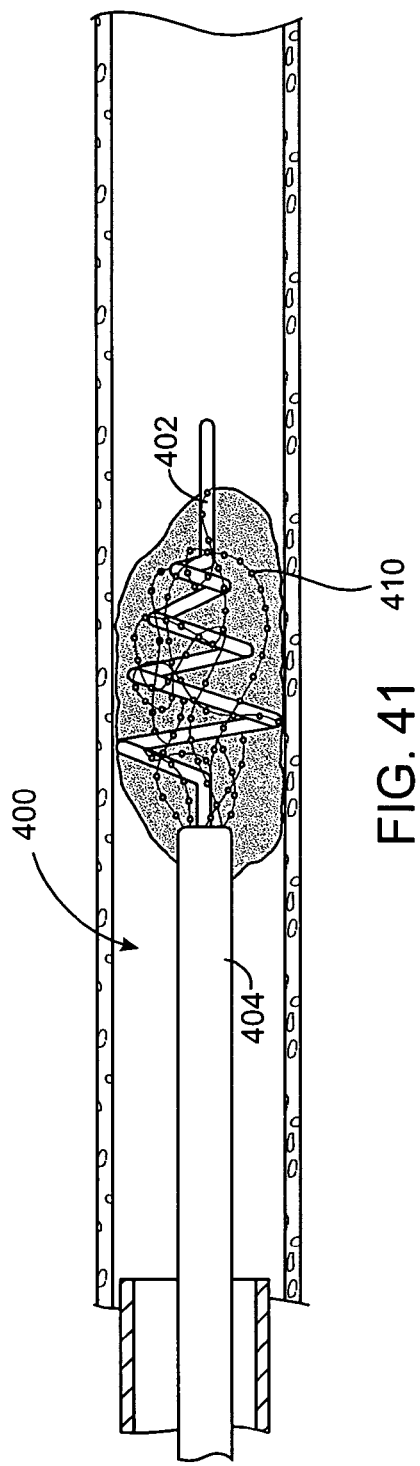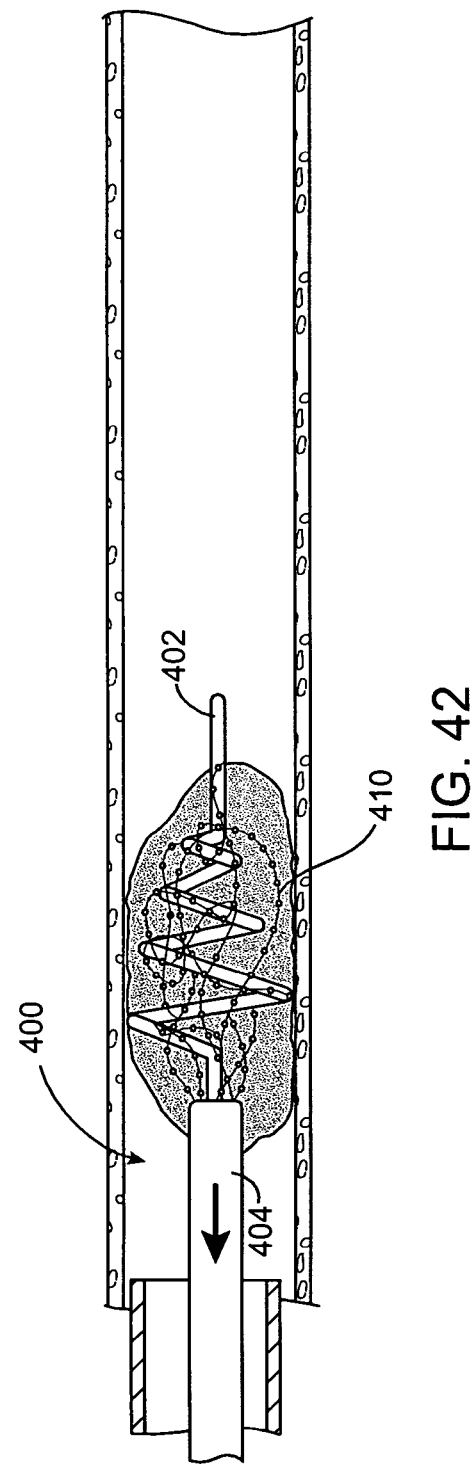

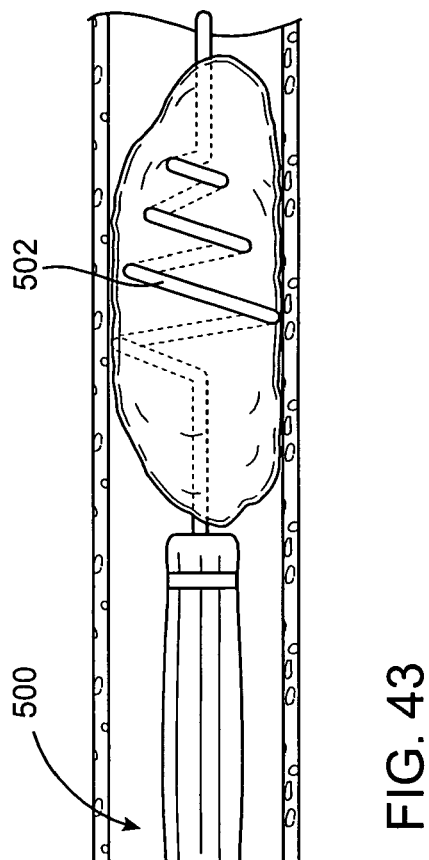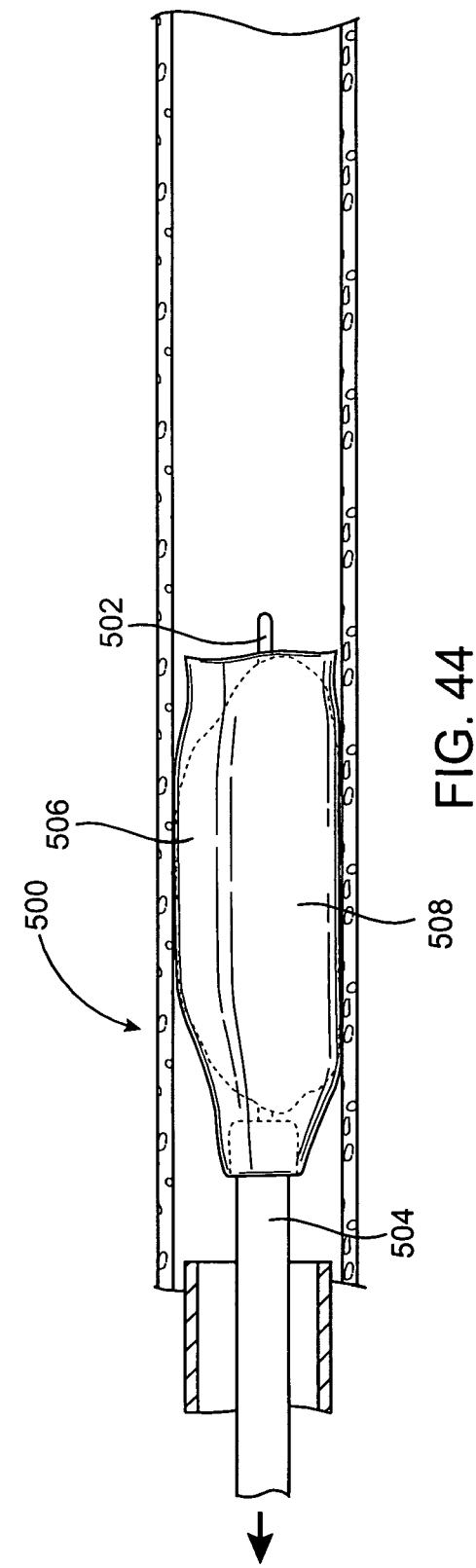
FIG. 43
FIG. 44

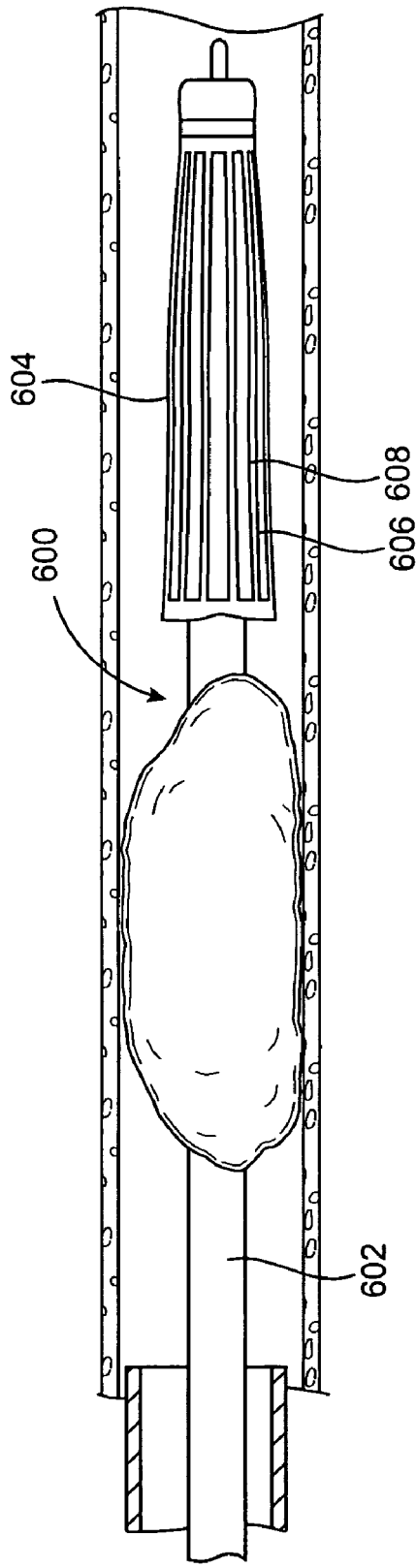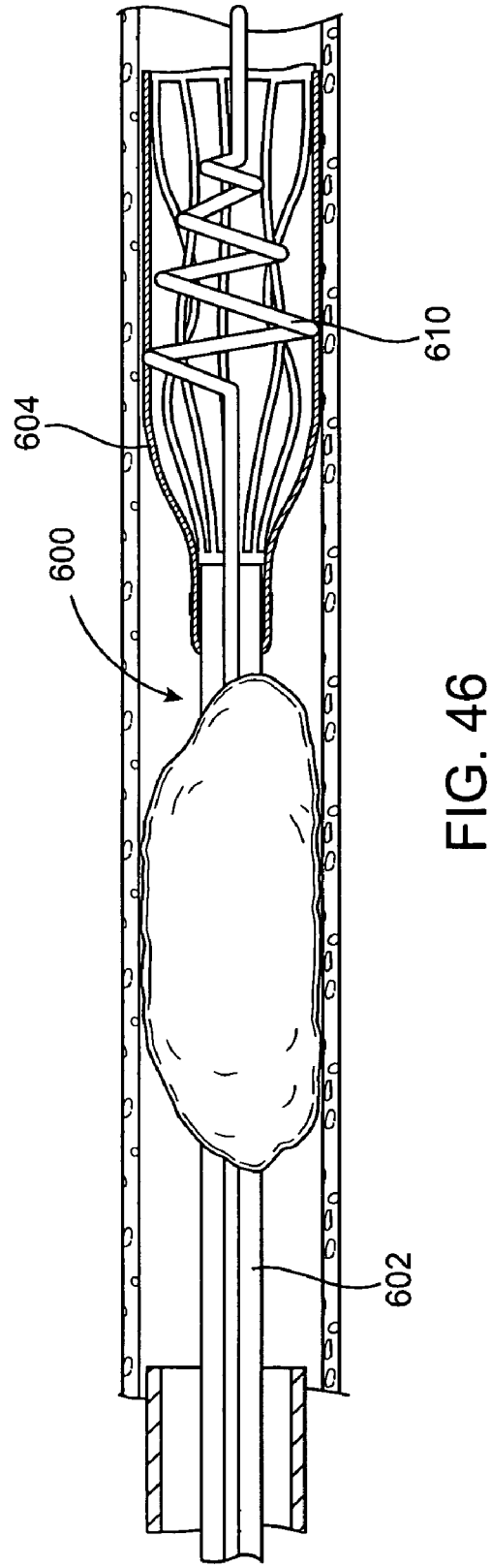

SYSTEMS, METHODS AND DEVICES FOR REMOVING OBSTRUCTIONS FROM A BLOOD VESSEL

CROSS-REFERENCE TO RELATED APPLICATIONS

The present application is a continuation of application Ser. No. 10/839,977, filed on May 5, 2004, now U.S. Pat. No. 7,766,921 which is a continuation-in-part of application Ser. No. 10/460,751, filed on Jun. 11, 2003 now abandoned, which is a continuation-in-part of application Ser. No. 10/055,714, filed Jan. 22, 2002 now U.S. Pat. No. 7,285,126 which is a continuation-in-part of application Ser. No. 09/891,141, filed Jun. 25, 2001 now U.S. Pat. No. 6,824,545, which is a continuation in part of application Ser. No. 09/756,476, filed Jan. 8, 2001 now U.S. Pat. No. 6,663,650, which is a continuation-in-part of application Ser. No. 09/605,143, filed Jun. 29, 2000 now U.S. Pat. No. 6,730,104, the full disclosures of which are incorporated herein by reference for all purposes.

BACKGROUND OF THE INVENTION

Field of the Invention

The present invention is directed to methods and devices for removing obstructions from blood vessels. The device may be used to retrieve and remove clots and other biological obstructions. The device may also be used to retrieve embolic coils and the like which have been misplaced or have migrated to an undesirable location.

One such obstruction removal device is disclosed in U.S. Pat. No. 5,895,398 which is hereby incorporated by reference. The device has an expandable engaging member which is introduced into the blood vessel to engage the obstruction for removal.

The present invention is also directed to devices, systems and methods which use an expandable capture element when removing obstructions from a blood vessel. One such system for removing obstructions in a blood vessel is described in U.S. Pat. No. 5,102,415 to Guenther et al. The system described in U.S. Pat. No. 5,102,415 has a balloon catheter and a catheter having an expandable tip which receives the obstruction. The balloon catheter is passed through the obstruction while the balloon is deflated. The balloon is then inflated and the tip of the catheter is expanded. The balloon is then moved proximally so that the obstruction is pulled into the expanded tip of the catheter. A problem with the system of U.S. Pat. No. 5,102,415 is that the interaction between the balloon catheter and the leading edge of the catheter may tend to shear off portions of the obstruction. This can cause obvious problems when working in sensitive vascular areas.

The present invention is directed to additional devices and methods for removing obstructions in a blood vessel.

SUMMARY OF THE INVENTION

In accordance with the present invention, device and methods for removing obstructions are provided. In a first aspect of the invention, an obstruction removal device is provided which has an obstruction engaging element extending from an insertion element. The engaging element is movable from a collapsed position to an expanded position. The engaging element forms coils having varying diameter wherein the coils at a distal portion are larger than coils at an intermediate portion. The distal portion forms a relatively closed structure which prevents the obstruction, or any part thereof, from migrating downstream. The distal portion is expanded distal to the obstruction while the proximal portion engages and holds the obstruction.

In another aspect of the present invention, another obstruction removal device is provided which has at least one closed loop and preferably two closed loops. The closed loop provides an advantage when advanced through a catheter or sheath in that the closed loop produces opposing radial forces on the catheter or sheath through which the loop is advanced. In this manner, the obstruction removal device can be advanced more easily through the catheter or sheath to prevent binding or kinking of the device during advancement. In a preferred embodiment, the obstruction removal device has two loops of varying diameter with the distal loop having a larger diameter. Each of the loops lie in a plane with the planes of the two loops preferably being perpendicular to one another.

Any of the obstruction removal devices described herein may also be used with a source of power coupled to the obstruction removal device for use as described below. The source of power may simply produce a positive or negative charge or may be an RF energy source. The source of power may be used to help the obstruction removal device penetrate and engage the obstruction and may also be used to adhere the obstruction to the obstruction removal device as will be described. In a preferred embodiment, a negative charge is provided when advancing the obstruction removal device into the obstruction and a positive charge, or RF energy, is supplied to adhere the device to the obstruction.

The devices of the present invention may be manufactured in any suitable manner. In another aspect of the present invention, the obstruction removal device has a core element surrounded by a sheath. A strand, preferably about four strands, are positioned between the core element and the tube. The strand and the tube prevent any part of the obstruction removal device from breaking free should the core element fail. The strand and tube will hold the obstruction removal device together even if the core element breaks. The sheath is preferably flexible so that the sheath can undergo much larger deflections than the core element.

The obstruction removal devices of the present invention may also be advanced through a guide catheter having a flow restricting element which is preferably a balloon but may be any other suitable structure. The flow restricting element is expanded to reduce blood flow through the obstructed vessel to minimize the likelihood that the obstruction will migrate downstream.

In another aspect of the invention, a system is provided which has an expandable capture element and an obstruction engaging device which together work to remove an obstruction from a blood vessel. The capture element is advanced through the patient in a collapsed position and is expanded when at the desired location. The obstruction engaging device preferably has one or more filaments which provide a relatively flexible interaction between the engaging device and the capture element. This provides advantages over the use of a balloon catheter as described in greater detail below. The obstruction engaging device preferably has 1-4 filaments and more preferably 1-2 filaments. Of course, the obstruction engaging device may have more filaments without departing from various aspects of the invention and, in fact, the device may form a filter which further helps to prevent portions of the obstruction from being carried downstream.

The capture element is preferably naturally biased toward the expanded position although the capture element may also be manually actuated as described below. The capture element has a support structure with a flexible cover attached thereto. The support structure preferably has a closed loop which opens the distal end of the cover. The loop is preferably integrally formed and has a number of integrally formed hinges which deflect when the loop is expanded and collapsed. The hinges are preferably V-shaped although other shapes may be used. A plurality of struts extend proximally from the loop.

The capture element may also be expanded by the user so that the user may select the appropriate time for expansion of the capture element. In this manner, the user may advance the capture element to a suitable location for expansion. The user may also collapse the capture element before withdrawing the capture element into a catheter. The capture element has an actuator for opening and closing the capture element. The actuator may have a control arm and a stable arm although any suitable actuator may be used. The control arm is manipulated to expand and contract a loop at the distal end of the capture element. Alternatively, the actuator may be a tube which cinches the loop closed. In a specific embodiment, the capture element may also evert when moving to the expanded position.

The device of the present invention may be used in various different locations and for various different purposes. In one embodiment, the device may be used in connection with a guide catheter. When used with the guide catheter, the device may be expanded to slow or even stop blood flow when performing other procedures downstream of the guide catheter such as removing a clot or placing a stent.

Alternatively, the device may be passed through a conventional guide catheter so that the device may be introduced further into the vasculature. In this system, the capture element passes through the guide catheter. The obstruction engaging device is then used to engage the obstruction and move the obstruction into the capture element.

In still another aspect of the invention, the capture element inverts when the obstruction is moved into the capture element. The obstruction is preferably engaged with an engaging element having a filament which ensnares the obstruction. The obstruction engaging element may be independent from the capture element or may be connected to the engaging element. The capture element inverts upon application of a compressive force to the inverting portion or upon any other suitable actuation force. The capture element preferably inverts when the compressive force is applied by either the obstruction or the engaging element.

In still another aspect of the present invention, a device and method for removing an obstruction from a blood vessel is provided. A strand extends along the elongate obstruction removing element and extends between the coils of the element. The element may be manipulated to entangle the main element with the strand and to entangle the device with the obstruction. The strand will become entangled with the element at locations dependent upon permitted expansion of the element within the blood vessel.

In yet another aspect, an intravascular device and method for removing material from a vascular site are provided. A filament is wrapped around the main element in a delivery condition. The filament and main element are then rotated relative to one another to cause the two to essentially unravel.

These and other advantages of the invention will become apparent from the following description, drawings and claims.

BRIEF DESCRIPTION OF THE DRAWING FIGURES

FIG. 1 shows a system for removing an obstruction.
FIG. 2 shows the obstruction removal device in a collapsed condition.
FIG. 3 shows the obstruction removal device with a distal portion of the obstruction section removal device expanded.
FIG. 4 shows the obstruction removal device with a proximal portion expanded to engage an obstruction.
FIG. 5 shows the capture element collapsed around the obstruction prior to withdrawal.
FIG. 6 shows the capture element contained within the catheter in an inverted position when collapsed.
FIG. 7 shows another device for capturing an obstruction.
FIG. 8 shows the capture device of FIG. 7 advanced at least partially into engagement with the obstruction.
FIG. 9 shows an obstruction engaging element advanced through the capture element.
FIG. 10 shows the element engaging the obstruction.
FIG. 11 shows the obstruction partially contained within the capture element.
FIG. 12 shows the obstruction completely contained within an inverted portion of the capture element.
FIG. 13 shows still another device for capturing an obstruction.
FIG. 14 shows the element engaging the obstruction.
FIG. 15 shows the inverting portion beginning to invert to capture the obstruction.
FIG. 16 shows the obstruction partially contained within the capture element.
FIG. 17 shows the obstruction completely contained within the capture element.
FIG. 18 shows the inverting portion contained within another catheter such as the guide catheter for removal from the patient.
FIG. 19 shows the distal end of the device of FIGS. 13-18 with the engaging element expanded.
FIG. 20 shows the distal end of the device of FIGS. 13-18 with the engaging element collapsed.
FIG. 21 shows another device for removing an obstruction.
FIG. 22 shows the device of FIG. 21 expanded within a blood vessel.
FIG. 23 shows another device for removing an obstruction in a collapsed position.
FIG. 24 shows one possible configuration for the expanded device of FIG. 23.
FIG. 25 shows another possible configuration for the expanded device of FIG. 23.
FIG. 26 shows a device having more strands and loops along the proximal section than along the distal section.
FIG. 27 shows the device having an interlocking strand extending between two strand loops.
FIG. 28 shows the strand loops interlocking closer to the distal and proximal ends in the upper and lower parts, respectively.
FIG. 29 shows the strands positioned within the expanded shape of the main element.
FIG. 30 shows the device positioned proximate to an obstruction.
FIG. 31 shows the device advanced into and through the obstruction.
FIG. 32 shows expansion of part of the main element distal to the obstruction.
FIG. 33 shows expansion of part of the main element within the obstruction.
FIG. 34 illustrates that rotation of the main element causes the strand to become entangled with the main element and enhances engagement between the device and the obstruction.
FIG. 35 shows still another device for removing an obstruction collapsed within the delivery catheter.
FIG. 36 shows the device in an expanded shape.

FIG. 37 shows the device of FIG. 35 with the filaments removed for clarity.

FIG. 38 shows the device of FIG. 36 with the filaments removed for clarity.

FIG. 39 shows still another device for removing an obstruction with a catheter having an interlocking structure.

FIG. 40 shows the interlocking structure entangled with an obstruction engaging element.

FIG. 41 shows the interlocking structure and element embedded within the obstruction.

FIG. 42 shows the interlocking structure and element being withdrawn.

FIG. 43 shows a catheter having a flexible tube to contain the obstruction.

FIG. 44 shows the obstruction contained within the catheter of FIG. 43.

FIG. 45 shows another catheter having a flexible tube which cooperates with the element to dislodge and capture the obstruction.

FIG. 46 shows the catheter and element entangled.

DETAILED DESCRIPTION OF PREFERRED EMBODIMENTS

Figure 1:
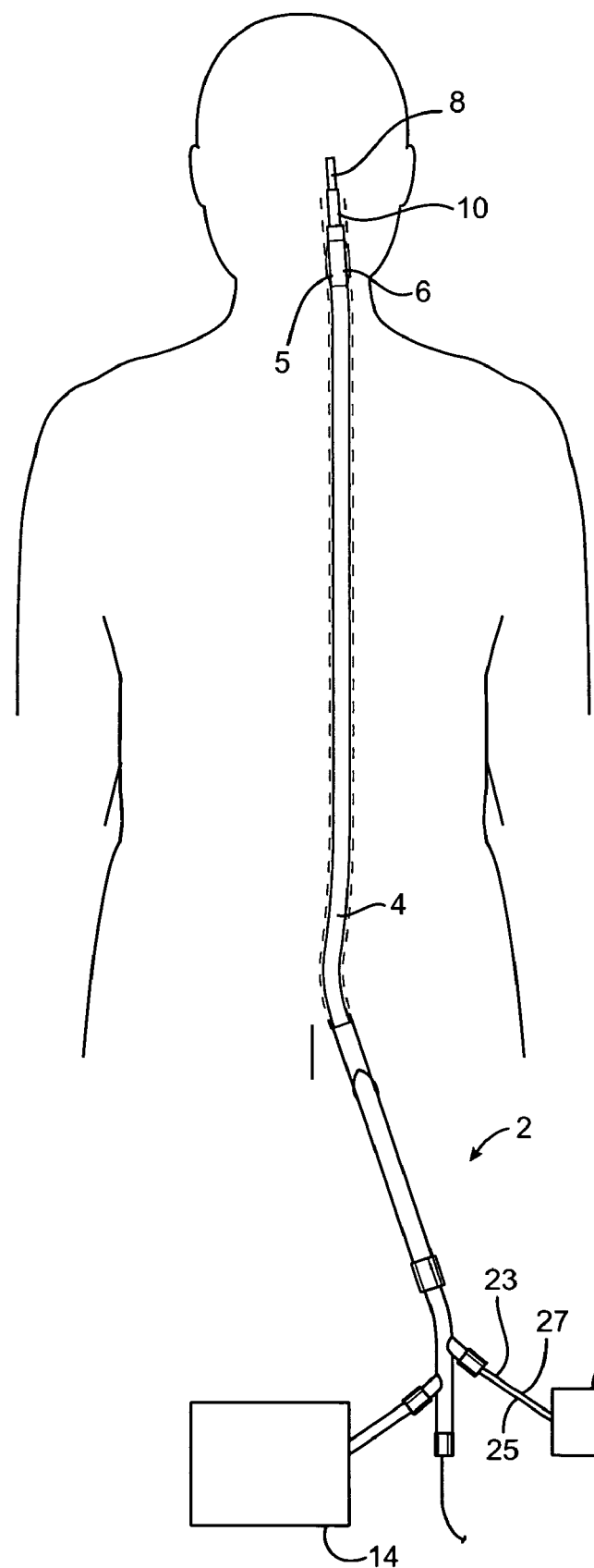

Referring now to FIGS. 1-4, a system 2 for removing an obstruction is shown. A guide catheter 4 is advanced to a location proximal to an obstruction. When accessing the cerebral vasculature, for example, the guide catheter 4 is often positioned in the carotid or vertebral artery. Of course, the guide catheter 4 may not be necessary or may be positioned in any other suitable location depending upon the location of the obstruction. The guide catheter 4 preferably has a flow restricting element 6 which restricts or even stops blood flow through the vessel as described below. The flow restricting element 6 is preferably a balloon 5 coupled to a source of inflation fluid 7 which is used to inflate the balloon 5.

An obstruction removing device 8 is advanced through the guide catheter 4 to the obstruction. A microcatheter 10 may also be positioned within the guide catheter 4 to deliver the obstruction removing device 8 further into the vasculature. The obstruction removing device may be advanced by itself through the microcatheter 10 or may be contained within a sheath 12 which is advanced through the microcatheter 10. A source power 14 may also be coupled to the obstruction removal device 8 for use in the manner explained below. The power source 14 may simply produce a positive or negative charge or may be an RF or other suitable power source.

Figure 3:
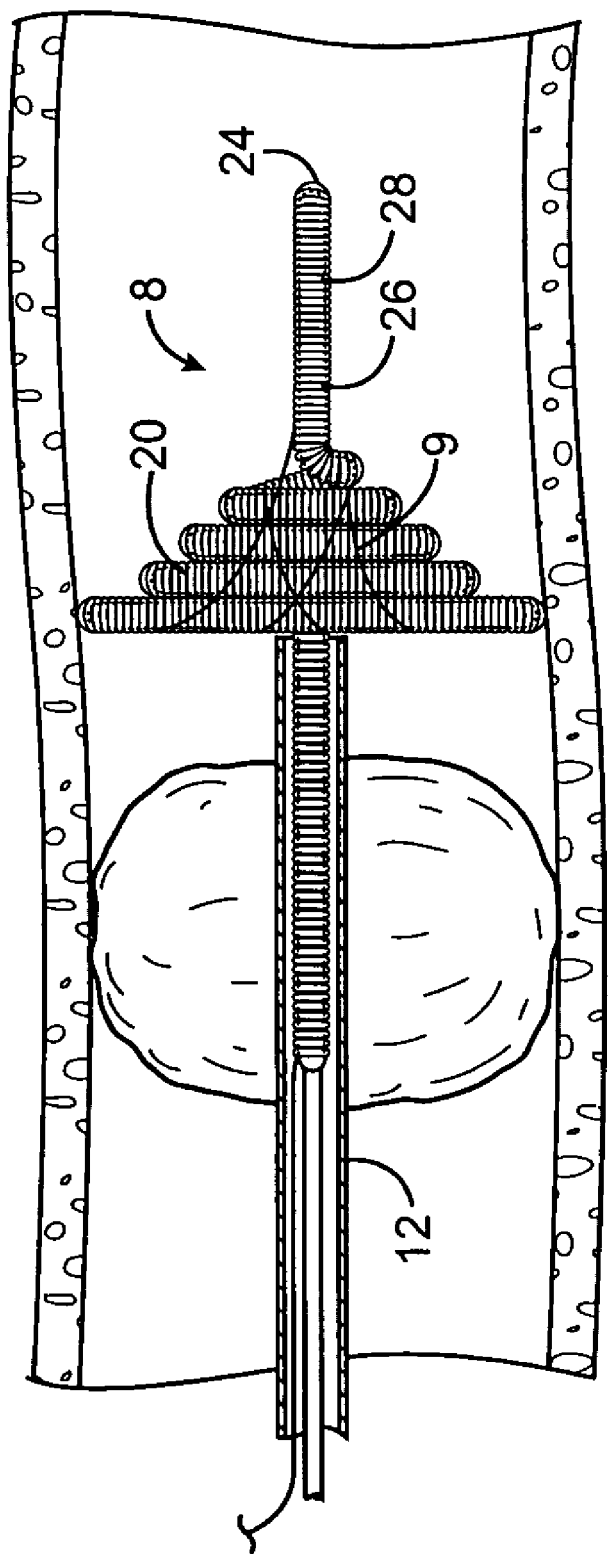
Figure 4:
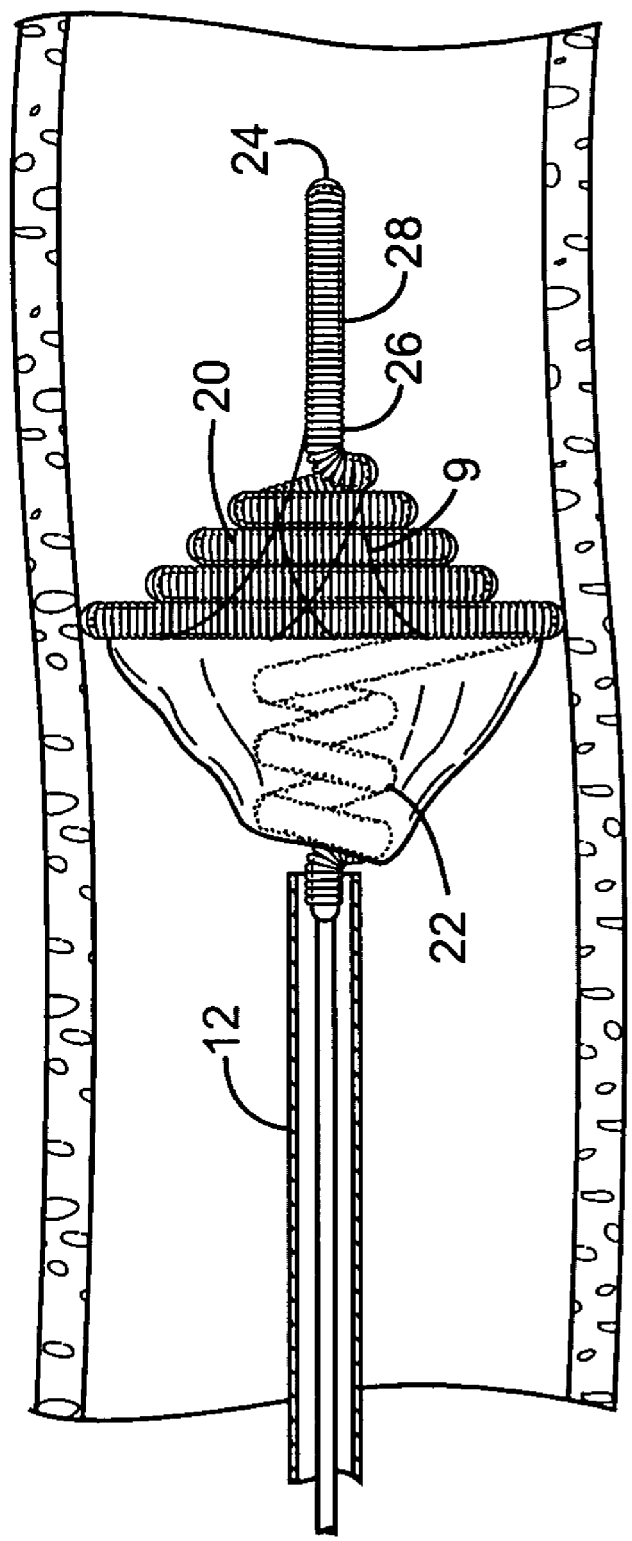
Figure 5:
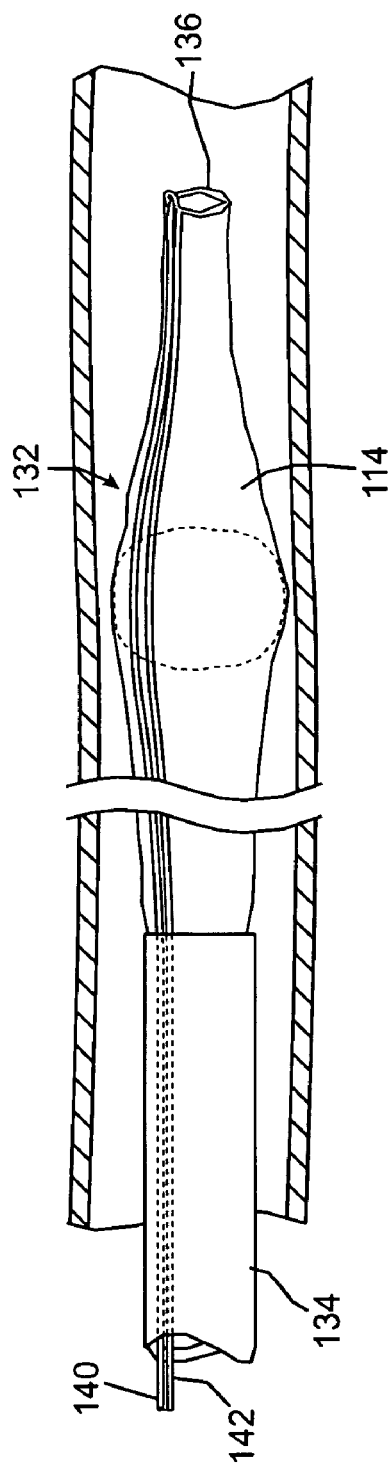

The obstruction removing device 8 has an engaging element 16 extending from an insertion element 18. The engaging element 16 is movable from a collapsed position (FIG. 2) to an expanded position (FIGS. 3 and 4). When the engaging element 16 is contained within the sheath 12 or microcatheter 10, the engaging element 16 is in a relatively straight configuration. The engaging element 16 has a distal portion 20, which forms a relatively closed structure, which can catch or trap the obstruction, or any part thereof, to prevent migration of the obstruction or part thereof. The engaging element 16 has a proximal portion 22 which is formed with smaller coils than the distal portion 20. The proximal portion 22 engages the obstruction as described below.

The engaging element 16 (FIGS. 2-4) preferably has a number of markers 23, 25, 27 (FIG. 1) which provide an indication as to how much of the engaging element 16 extends from the sheath 12 or microcatheter 10. For example, markers 23, 25, 27 may indicate when the engaging element 16 is about to be exposed or is ½, ¾ or fully exposed. In this manner, the user may quickly advance the engaging element 16 through the sheath 12 or microcatheter 10 without inadvertently exposing and advancing the engaging element 16 out of the sheath 12 or microcatheter. The markers 23, 25, 27 can also be used to provide a controlled diameter of the engaging element 16 since the diameter of the engaging element 16 is known for the various positions corresponding to the markers 23, 25, 27. The markers 23, 25, 27 may also be used to size the vessel in which the engaging element 16 is positioned by observing when the engaging element 16 engages the vessel walls and determining the size of the engaging element 16 using the markers 23, 25, 27.

The insertion element 18 is preferably made of a superelastic material or stainless steel having a diameter of 0.004 to 0.038 inch and preferably about 0.010 inch. Although the insertion element 18 is preferably a solid, elongate element, the insertion element 18 may take any other suitable structure such as a hollow tube. The engaging element 16 is preferably made of a superelastic material, such as nitinol, and has a diameter of 0.005-0.018 inch, more preferably 0.005-0.010 inch and most preferably about 0.008 inch. The engaging element 16 has a rounded, atraumatic tip 24 to prevent damage to the vessel and facilitate advancement through the vessel, microcatheter 10 and/or sheath 12. A radiopaque wire 26, such as platinum ribbon 28 having a width of 0.004 inch and a thickness of 0.002 inch, is preferably wrapped around the engaging element 16 to improve radiopacity.

The device 8 is preferably self-expanding but may also be expanded with an actuator 29. The actuator 29 is preferably a thin filament which is tensioned to move the device 8 to the expanded position. An advantage of the invention is that the filament 29 extends through the same lumen as the device 8 thereby minimizing the overall size of the device. It is understood that throughout discussion of the devices and methods herein that any of the devices may be expanded using the actuator 29 rather than being self-expanding without departing from the scope of various aspects of the invention.

The device 8 may also include a cover 9 which extends between adjacent coils. The cover 9 may be a number of individual strands 11 which extend between the coils or may be an elastic membrane which covers the coils. The strands 11 are preferably elastic to stretch when the device 8 is expanded.

Use of the obstruction removing device 8 is now described. The guide catheter 4 is introduced into the patient and delivered proximal to the target vessel such as to the carotid or vertebral artery. The microcatheter 10 is then advanced through the guide catheter 4 further into the vasculature to a position proximal to, within or distal to the obstruction. The obstruction removal device 8 is then advanced through the microcatheter 10 either by itself or pre-loaded within the sheath 12. The obstruction removal device 8 is then advanced to the obstruction. Before advancing the obstruction removal device 8 further, the flow restricting element 6 on the guide catheter 4 is expanded to reduce and even stop flow through the vessel. Stopping flow in the vessel may help prevent the obstruction, or any parts thereof, from migrating downstream. Reducing flow through the vessel may also reduce the likelihood that the obstruction is disrupted by a combination of flow and the obstruction removal device 8.

The obstruction removal device 8 is then placed into the obstruction and preferably through the obstruction. The engaging element 16 is then advanced out of the microcatheter 10 or sheath 12 to permit the distal portion 20 of the engaging element 16 to expand at a location beyond the obstruction. In this manner, the relatively closed distal portion 20 prevents the obstruction, or any part thereof, from migrating downstream. The proximal portion 22 is then advanced out of the sheath 12 or microcatheter 10 so that the smaller coils of the proximal portion 22 engage the obstruction as shown in FIG. 4.

The power source 14 may be also be used with any of the obstruction removal devices in the following manner, however, the methods and devices of the present invention may, of course, be practiced without the power source 14. As mentioned above, the power source 14 may simply produce a charge at the engaging element 16 or may be a source of RF energy. In one particular method of the present invention, the power source 14 produces a negative charge while advancing the engaging element 16 through the obstruction. The negative charge may aid in passing the engaging element 16 through the obstruction and may help to dissolve part of the obstruction. The power supply is then changed to produce a positive charge to adhere the obstruction to the engaging element 16. Alternatively, the power source 14 may be an RF energy 1I source, which delivers RF to the engaging element 16 which also adheres the obstruction to the engaging element 16 and may help provide a controlled penetration into the obstruction. The obstruction is then removed by moving the obstruction into the guide catheter 4, which is then withdrawn to remove the obstruction. Use of the power source 14 is particularly useful when the obstruction is a biologic structure such as a clot.

Figure 6:
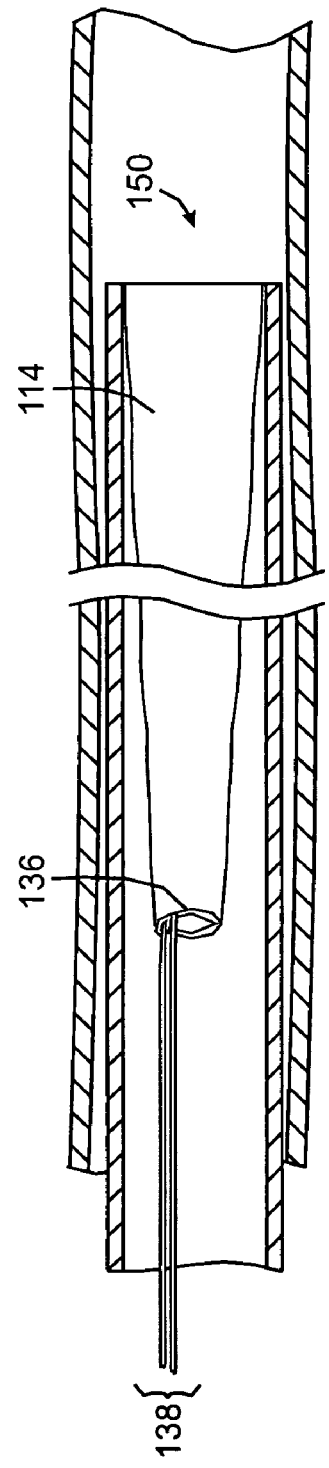
Figure 9:
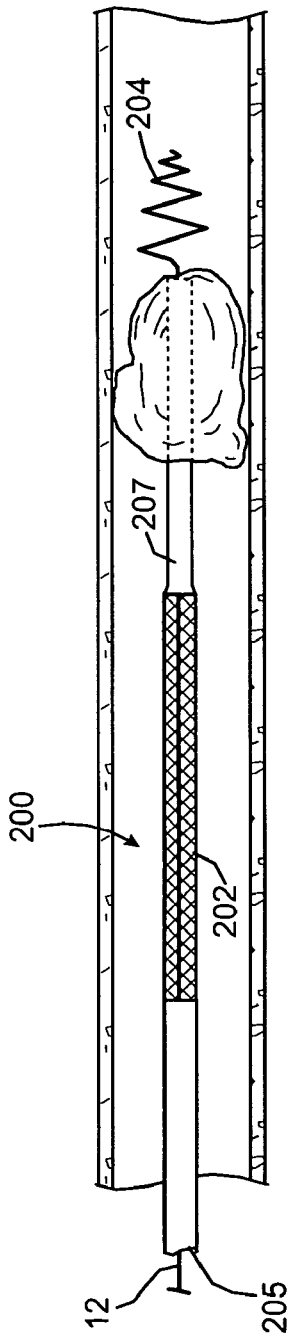

Referring to FIG. 6, a capture element 150 is shown. The capture element 150 has a cover 114 and an actuator 138 which includes a stable arm 142, a control arm 140, and a loop 136 although other actuating structures may be used. The capture element 150 is contained within the catheter 107 or the guide catheter 4 during introduction and is then everted out of the catheter 107 or catheter 4 when deployed. After the obstruction is contained within the capture element 150, the capture element 150 is withdrawn into the catheter 4. Although it is preferred to withdraw the capture element 150 into the catheter 4, the capture element 150 may be collapsed and then inverted back into the catheter 134 thereby trapping the obstruction in the catheter 134 itself.

The capture element 150 is opened and closed by manipulating the arms 140, 142 to open and close the loop 136. The obstruction is captured with the element 150 by itself or together with an obstruction engaging element as described herein Referring to FIGS. 7-12, another capture element 200 is shown for capturing an obstruction. The capture element 200 has an inverting portion 202 that inverts to entrap the obstruction. The capture element 200 is then withdrawn into the guide catheter 4 (FIG. 1) for removal of the obstruction from the patient.

Figure 10:
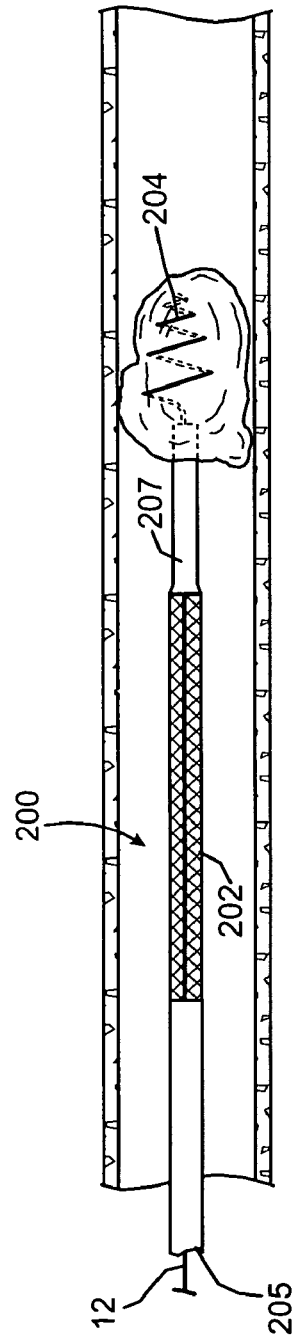

Referring to FIG. 10, the engaging element 204 is shown engaging the obstruction. The element 204 may be any suitable element such as the obstruction engaging elements and removal devices described herein. The element 204 passes through a lumen 205 in the capture element 200. The engaging element 204 may be advanced through the capture element 200 by itself or may be contained within the microcatheter 10 or sheath 12 (FIGS. 1 and 2) which is advanced through the capture element 200.

The capture element 200 has a distal portion 207 which is flexible and which may be partially contained, engaged or otherwise in contact with the obstruction as shown in FIG. 8. The distal portion 207 may also invert but preferably does not invert. The distal portion 207 necks-down at a distal end 209 to a size smaller than the guidewire GW so that the capture element 200 is advanced together with the guidewire. Of course, the capture element 200 may also be advanced by itself after introduction of the guidewire and may be contained within or advanced over another catheter without departing from the invention.

Figure 11:
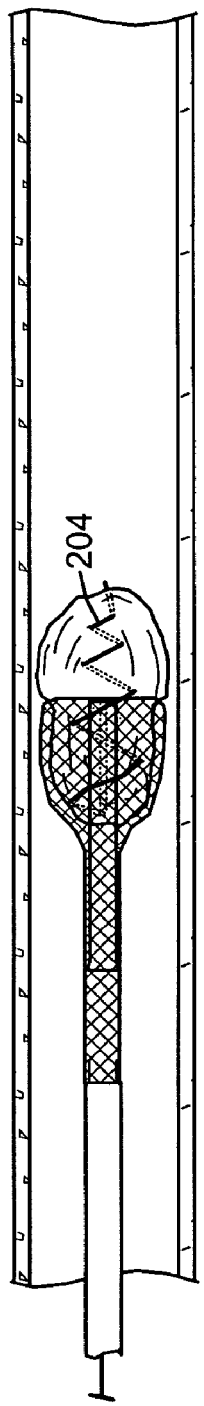
Figure 12:
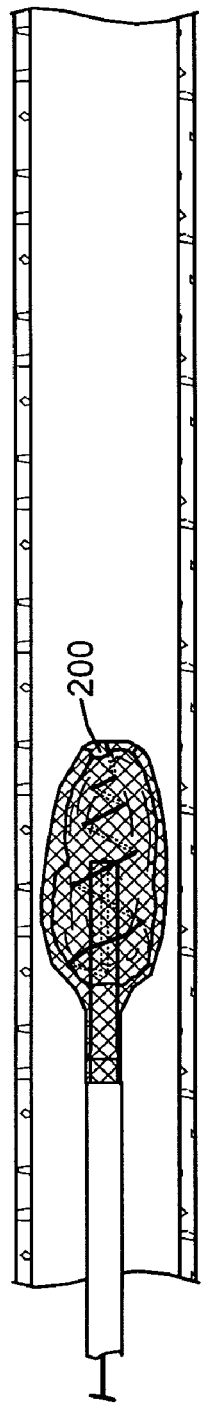
Figure 13:
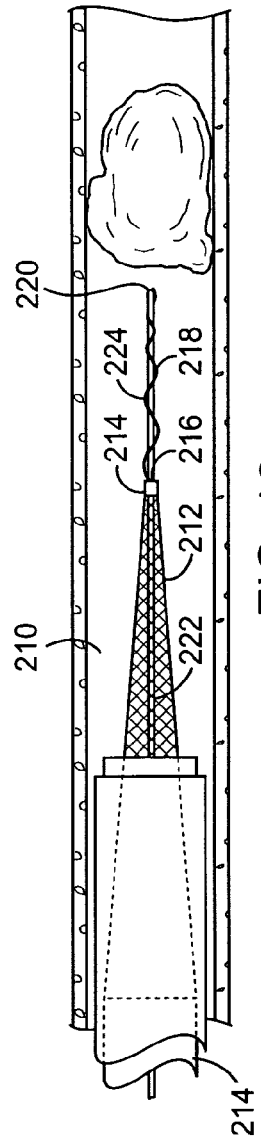
Figure 14:
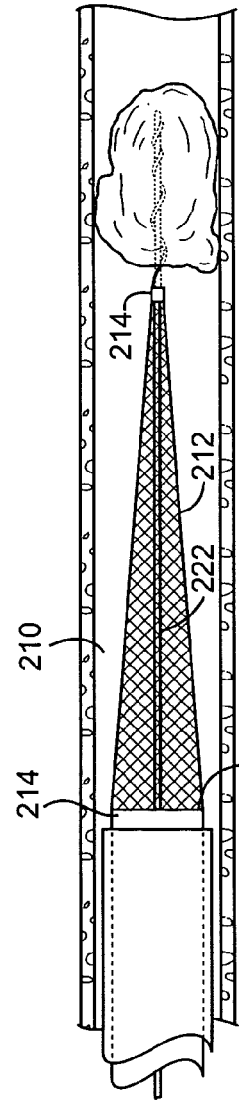
Figure 15:
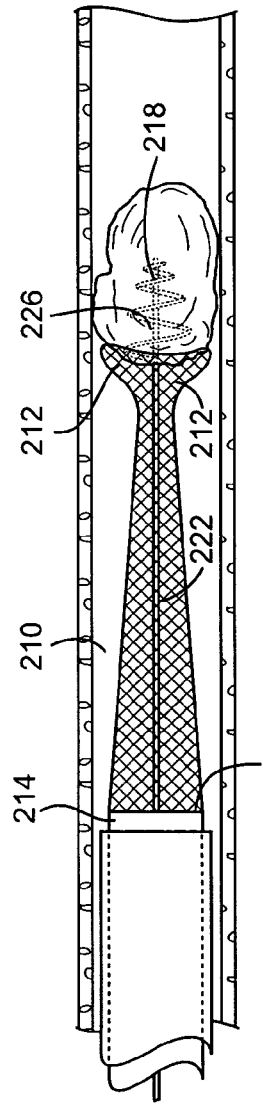
Figure 19:
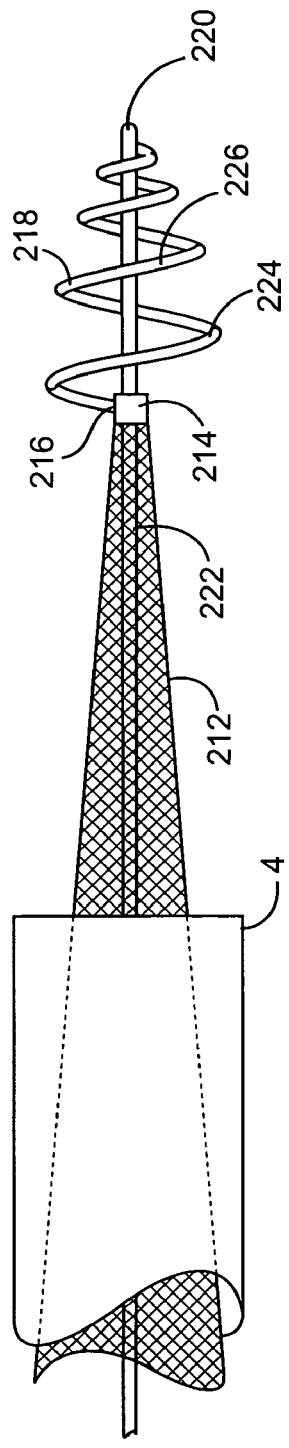
Figure 20:
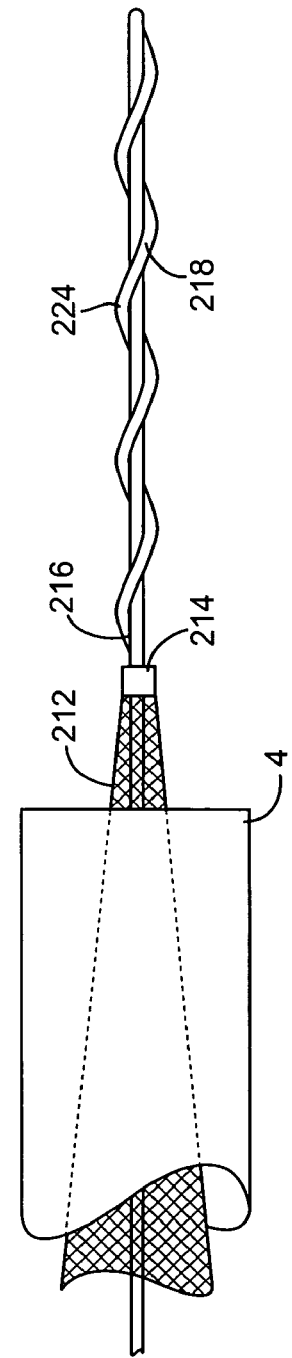

The element 204 engages the obstruction in any suitable manner. The inverting portion 202 is then inverted by applying a compressive force to the inverting portion 202. The compressive force is applied by moving the capture element 200 relative to the engaging element 204 which causes the element 200 and/or obstruction to compress the inverting portion. Continued relative movement moves the obstruction into the inverted capture element 200 as shown in FIGS. 11 and 12 to capture the obstruction. The capture element 200 is then moved into the guide catheter 4 (FIG. 1) for removal from the patient. The capture element 200 may be made of any suitable materials. For example, the distal portion 207 may be made of any suitable polymeric material such as those described herein and the inverting portion 202 may be made of a braided or woven material or fabric made of fibers or filaments of nitinol, stainless steel, polymer or other material.

Referring to FIGS. 13-20, another capture element 210 for removing an obstruction is shown wherein the same or similar reference numbers refer to the same or similar structure. The capture element 210 also has an inverting portion 212 connected to an end 213 of a delivery element 214 which may be a hollow tube, sheath or catheter. The distal end of the capture element 210 has a collar 214 attached to a proximal end 216 of an engaging element 218. A distal end 220 of the obstruction engaging element 218 is attached to an inner element 222 such as a wire, mandrel or guidewire. The collar 214 slides over the inner element 222 so that when the inner element 222 and delivery element 214 are movable relative to one another. Relative movement between the inner element 222 and delivery element 214 moves the obstruction engaging element 218 between the expanded and collapsed positions (FIGS. 19 and 20) and also can collapse the capture element 210. The engaging element 218 is similar to the other elements and devices described herein in that the element has a filament 224 which is tensioned to collapse the filament 224. The filament 224 forms coils 226 around the inner element 222.

Figure 2:
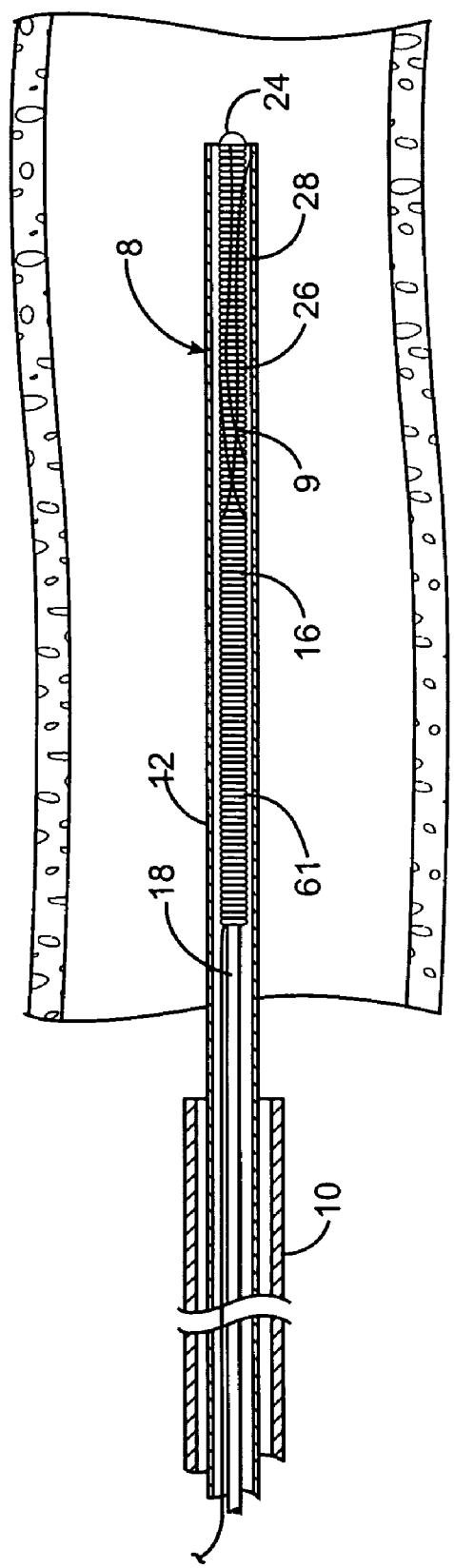

The capture element 210 and obstruction engaging element 218 are advanced through the patient in either the sheath 12 or microcatheter 10 (FIGS. 1 and 2). The capture element 210 and obstruction engaging element 218 are then positioned distal to the obstruction and the obstruction is engaged with the element 218. The capture element 210 and engaging element 218 are then moved relative to one another to invert the capture element 210 as described above.

Referring to FIGS. 21-29, still another device 902 for removing an obstruction is shown. The device 902 has a main element 904 that may be any suitable element 904 such as those described herein. The element 904 is held in a substantially straight, collapsed position within the delivery catheter 905 as described above. Similar to the embodiment of FIGS. 2 and 3, the element 904 has one or more strands 906 which extend along the element 904. Of course, the strands 906 may extend freely alongside the main element 904 or may be wound helically, interwoven or interlocked with the element 904 without departing from the scope of the invention. The strands 906 are tied, knotted, looped, soldered, or otherwise attached to the main element 904 at the ends of the expandable portion of the main element 904. Of course, the strands 906 may be looped around or attached to the main element 904 at other parts of the main element 904. For example, the strand 906 may be attached or coupled to the main element 904 several centimeters proximal to the expandable portion of the main element 904 without departing from the scope of the invention.

Figure 22:
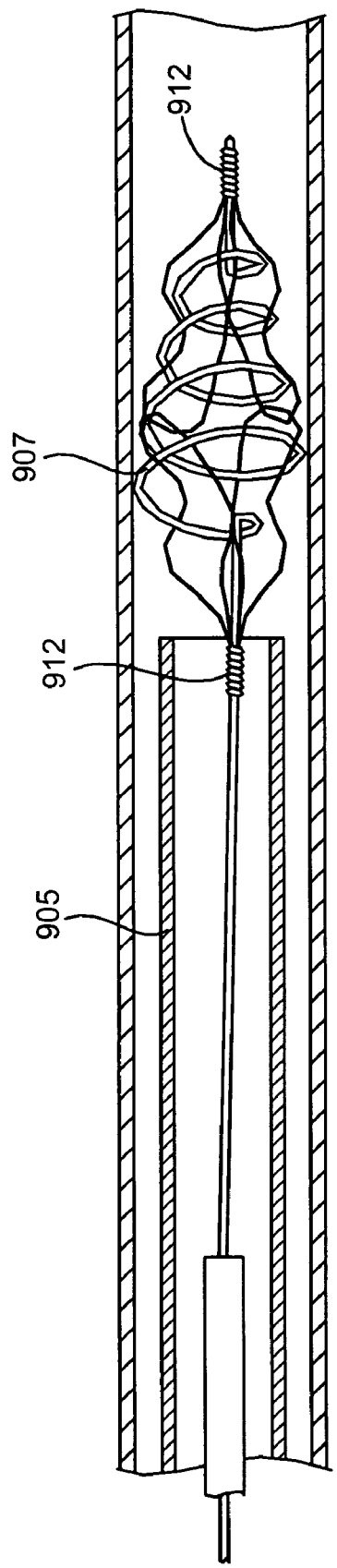
Figure 28:
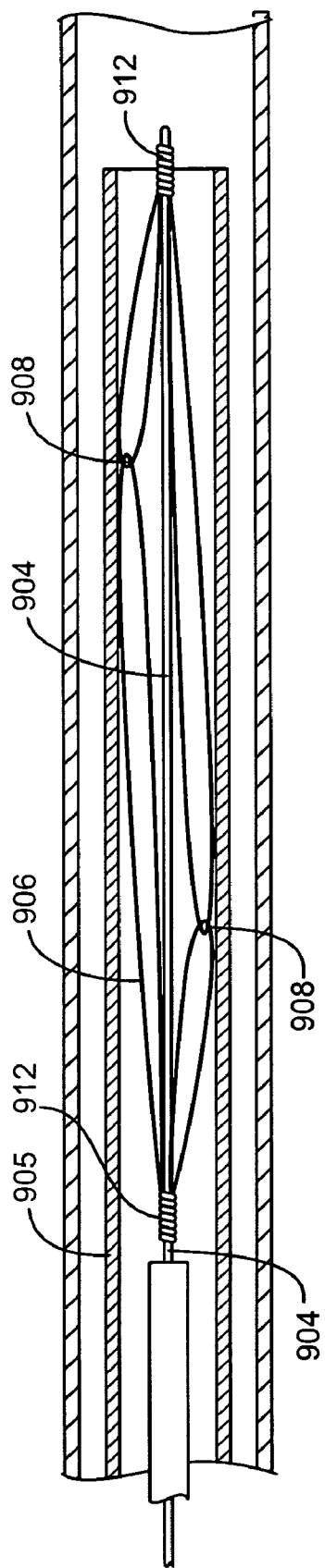

The main element 904 may be any suitable element 904 which is naturally biased toward the expanded position such as any of the elements described herein. FIGS. 22, 24 and 25 show three different embodiments of the main element 904 for purposes of illustration. The main element 904 may form helical coils 907 having varying diameter as shown in FIG. 22 or may have coils 907 with the same diameter as shown in FIG. 25 or may even have coils 907 which extend transverse to the longitudinal axis as shown in FIG. 24. Of course, any suitable shape may be used for the main element 904. Any of the devices described herein may have a main element which extends transverse or perpendicular to the longitudinal axis as shown in FIG. 24 and as further shown below in connection with FIG. 36. Thus, the embodiment of FIG. 29, for example, may have the coils extending transverse to the longitudinal axis.

Figure 21:
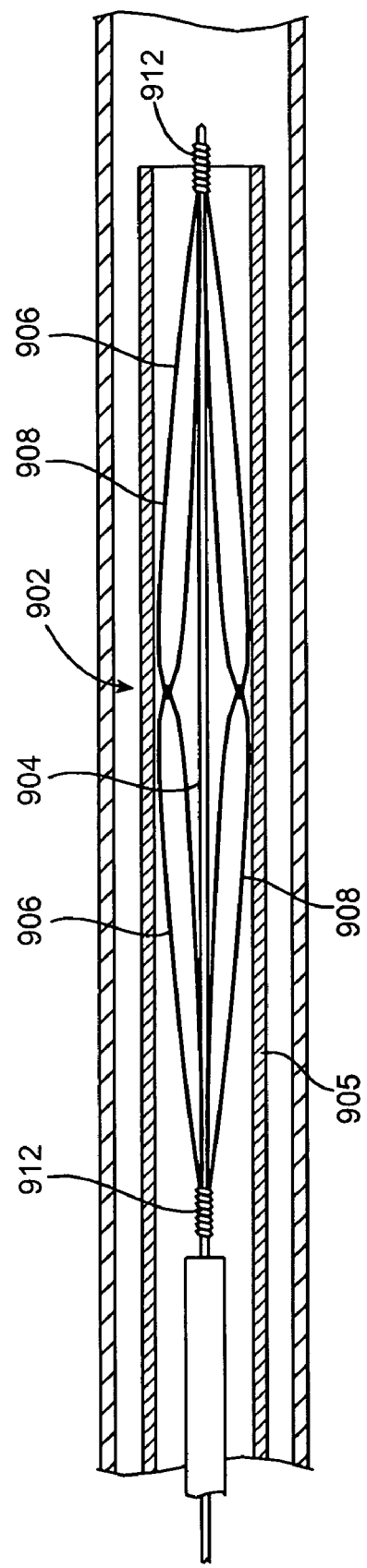

The strand 906 may be any suitable filament, wire, fiber, monofilament and may be made of any suitable material such as nylon, polypropylene, polyester, polyurethane, silicone, latex, a liquid crystal polymer (LCP) such as Vectran or even nitinol or stainless steel. The strand 906 is flexible and may or may not have a predetermined shape with the strand 906 being deformed and deflected by the element 904 as the element 904 expands. The element 904 includes two strands 906 which interlock or have interlocking loops 908 at about the midpoint of the expandable portion of the element 904. Stated another way, the strands 906 form two loops 908 which interlock at the midpoint as shown in FIG. 21. The strands 906 and loops 908 are shown in an exaggerated state in the collapsed position of FIG. 21 for clarity. Of course, one advantage of the invention is that the strands 906 are relatively small and flexible and do not take up much space in the lumen of the delivery catheter as compared to conventional structures using wires and the like. This feature cannot be appreciated, of course, in the exaggerated depiction of FIG. 21.

Figure 29:
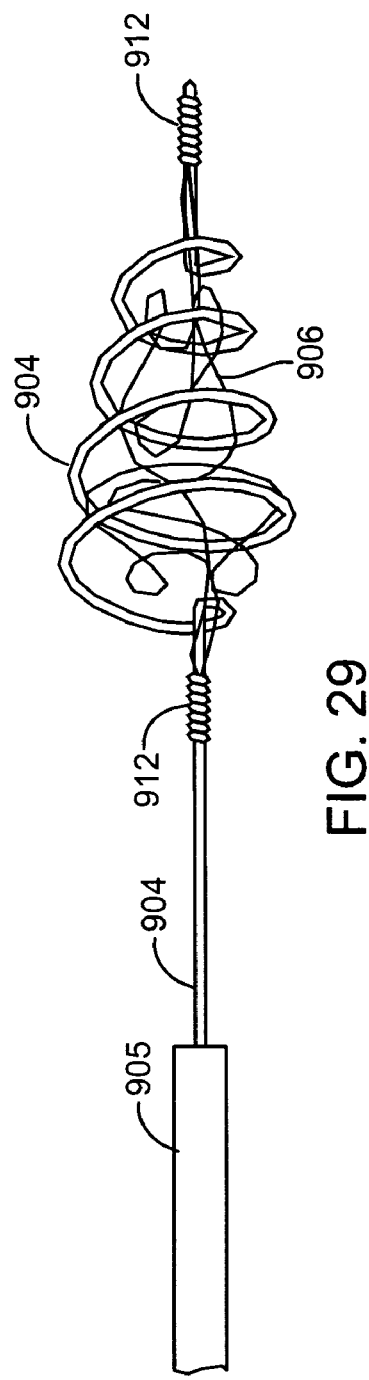

Referring to FIG. 26, the strands 906 may also form more loops 908 on one side than on the other. An interlocking loop 910 extending around the main element 904 may also be provided to interlock pairs of loops 908 as shown in FIG. 27. The strands 906 or loops 908 may also intersect nearer to the proximal or distal ends as shown in the upper and lower parts of FIG. 28. Referring to FIG. 29, the strands 906 may also be positioned generally inside the element 904 when the element 904 is expanded. The device may be loaded by pulling the ends of the element 904 when in the position of FIG. 25 to collapse the main element 904 around the strands 906. The device is then restrained in the delivery catheter 905 and delivered to the obstruction.

Referring again to FIGS. 22-25, the main element 904 may have a filament 912, such as platinum coil, wound around the expandable portion of the main element 904. The filament may help to improve radiopacity and may also be sized and configured so that the strand 906 can be held between adjacent windings of the filament 912 to enhance interlocking engagement between the strand 906 and element 904. Alternatively, the filament 912 may only be provided at the ends of the expandable portion of the main element 904 as shown in FIG. 22 where the strands 906 are coupled to the main element 904.

Figure 32:
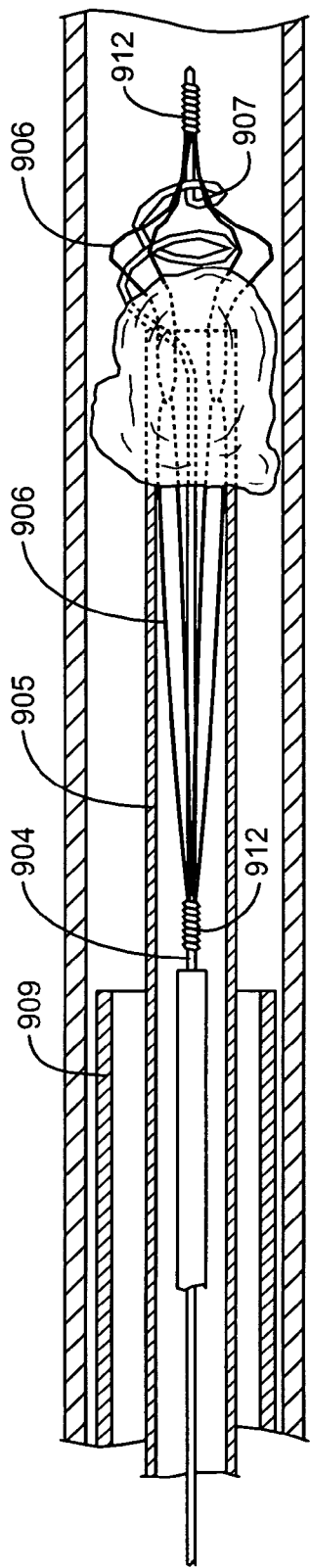
Figure 33:
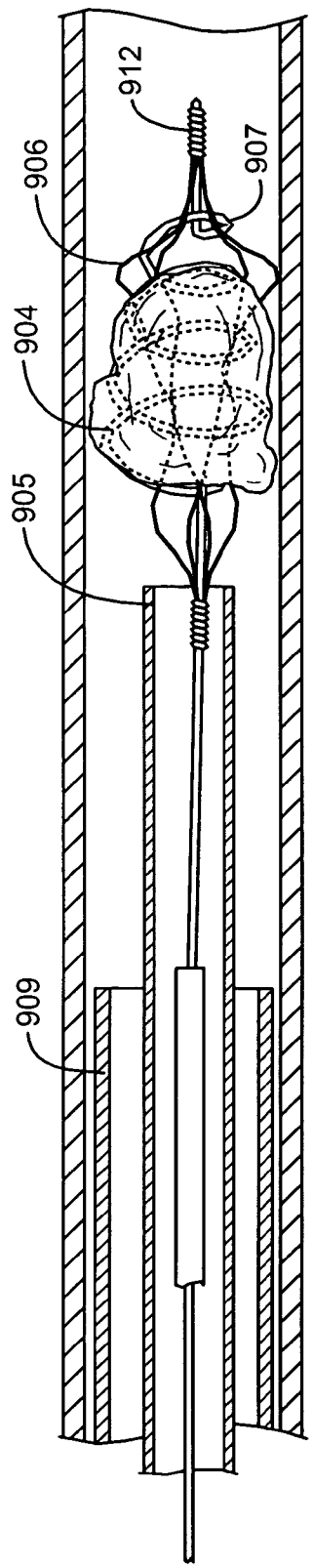
Figure 34:
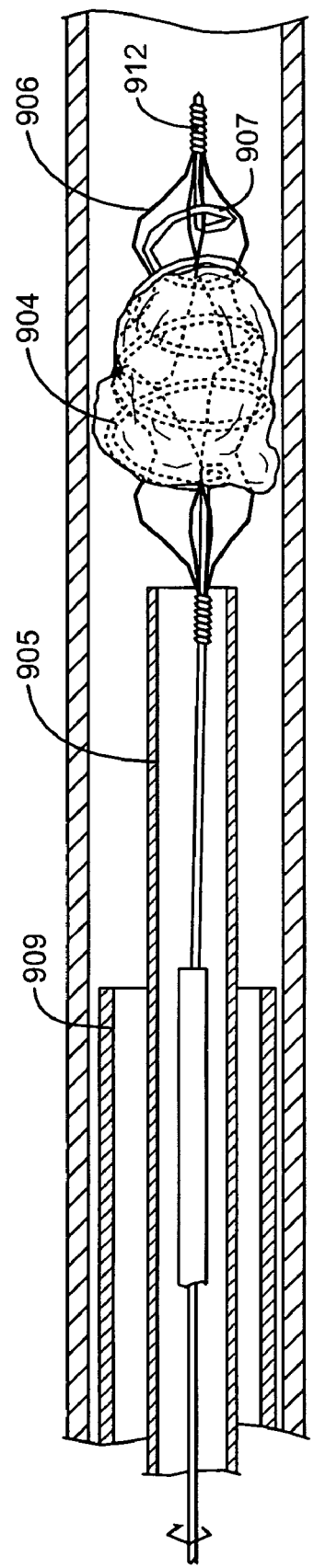

Use of the devices 902 of FIGS. 21-29 is now described with further reference to FIGS. 30-34. The delivery catheter 905 is passed through the obstruction so that the distal tip is beyond the obstruction as shown in FIG. 31. The main element 904 is then expanded so that one or more coils are distal to the obstruction as shown in FIG. 32. The delivery catheter 905 is then withdrawn further to expose more of the expandable portion of the main element 904 as shown in FIG. 33. Although it is preferred to position one or more coils distal to the obstruction, all or part of the expandable portion of the main element 904 may be expanded within, distal or even proximal to the obstruction without departing from the scope of the invention.

The device 900 may emerge from the delivery catheter 905 with the strands 906 being relatively free of the main element 904 between the proximal and distal attachments to the main element. Of course, the strands 906 may be interwoven, looped around or even somewhat entangled with the main element 904 so long as the user may manipulate the device to further entangle the strand 906 and element 904. Rotation of the device causes the strands 906 to become entangled with the main element 904 in a manner dictated by the geometric restrictions of the vessel and obstruction. The device itself may also become more entangled with the obstruction during rotation of the main element 904. An advantage of using the helical or coiled structures described herein is that rotation of the main element 904 not only causes the device to engage the obstruction but also causes the strand 906 to become entangled with the main element 904.

Another aspect of the present invention is that the amount of entanglement between the strand 906 and element 904 may be controlled. For example, the user may first attempt to remove the obstruction with little or no rotational manipulation of the element 904. The user can then pull on the main element 904 and determine whether the device can remove or dislodge the obstruction or whether the main element is disengaging or slipping relative to the obstruction. Disengagement can occur due to excessive elongation or distortion of the main element 904 or may be simply due to poor engagement between the device and obstruction. The user may then rotate or otherwise manipulate the device to cause further entanglement between the strand 906 and element 904 and between the device itself and the obstruction. Increasing the entanglement between the strand 906 and main element 904 may help to reinforce the main element which can reduce stretching and distortion of the main element 904 when the main element 904 is tensioned. The strands 906 also increase the overall surface area of the device and generally reduce the size of interstitial spaces in the main element 904. Another aspect of the present invention is that the strand 906 and element 904 may engage one another at locations dependent upon the permitted expansion of the main element 904 within the vessel. As such, the present invention provides advantages over conventional mesh-like structures having a predetermined geometry since these structures may not perform adequately under a variety of different size restrictions in an obstruction.

Although the strand 906 and element 904 may not be substantially entangled when the element is initially expanded, the main element 904 and strand 906 may also be designed to become entangled with one another during expansion of the main element 904. For example, the element 904 may naturally begin to twist in a helical manner to form coils 908 when expanding due to the shape of the element 904. The twisting motion causes the strand 906 to engage, contact and and/or otherwise entangle itself with the element 904 and obstruction. The strand 906 will engage the element 904 at a number of locations dependent upon the manner in which the element expands within the vessel as described above. Although the element 904 generally follows a helical path when expanding, the element 904 may expand in any other manner which tends to entangle the strand 906 and element 904. For example, the element 904 may rotate one way and then another or may be longitudinally displaced or reciprocated. Thus, it can be appreciated that the element may expand in a number of different ways to cause the strand 906 to become entangled with the element. Of course, the element may also be rotated or otherwise manipulated to enhance entanglement between the strand 906 and element even after expansion of the main element to provide the advantages described above.

After the obstruction has been engaged by the device, the main element is pulled to dislodge the obstruction for removal as describe above. Once the element has dislodged the obstruction, the obstruction may be moved into a guide catheter 909 or sheath for removal from the patient. The guide catheter 909 may have a balloon to occlude blood flow during withdrawal of the obstruction.

Referring now to FIGS. 35-38, still another device 300 for removing an obstruction from a vascular location is shown. The device 300 includes a main element 302 having a self-expanding portion 304 which forms a number of coils 306. Of course, the element 302 may take other shapes when expanded such as those described herein and incorporated by reference. The coils 306 may be oriented at an angle of about 90 degrees with respect to a longitudinal axis of the element 302 or may be oriented in any other manner such as parallel to the longitudinal axis. The coils 306 may have substantially the same diameter or the diameter of the coils 306 may vary in any suitable manner. The device 300 has one or more filaments 308 extending alongside the coils 306 similar to other devices described herein such as the devices of FIGS. 1-4 and 21-34. FIGS. 37 and 38 show only the element 302 and catheter 309 for clarity while FIGS. 35 and 36 show both the element 302 and filaments 308.

The filaments 308 are coupled to the main element 302 at proximal and distal locations 310, 312. The filaments 308 may be coupled to the element 302 at non-expanding portions just proximal and distal to the self-expanding portion 304 or the filaments 308 may be coupled to the expanding portion 304 of the element 302 such as the coils 306. The filaments 308 are preferably free to slide at the proximal location and are looped around the main element 302 to permit sliding. The filaments 308 are fixed at the distal location by securing the filaments 308 between windings of a radiopaque wire wrapped around the main element 302 at the distal end (see radiopaque wire 26 of FIG. 2). Other devices described herein, such as the devices of FIGS. 21-34, may have filaments which are slidable on the main element. For example, the wire 912 may be slidable on the main element so that all of the filaments 906 are coupled together and slidable on the main element 904. Alternatively, of course, the filaments may be independently slidable on the main element by simply looping the filaments around the main element as described above.

Use of the device of FIGS. 35 and 36 is now briefly described and all methods of using the devices described in connection with FIGS. 1-4 and 21-34 are incorporated here. The guidewire (see FIG. 1) is initially advanced through the obstruction and the catheter 309 is then advanced into or through the obstruction over the guidewire. The self-expanding portion 304 is then permitted to expand by either advancing the element or retracting the catheter 309. The expanding portion 304 of the main element 302 may be deployed distal to the obstruction or may be partially or entirely deployed within the obstruction. As the element 302 and filaments 308 are deployed, the element 302 and filaments 308 interact with one another and with the obstruction as the element 302 expands. The manner in which the filaments 308 deploy and contact the main element 302 and obstruction is dependent upon various factors including the geometry of the vessel and obstruction and the manner in which the element 302 expands as explained above. The filaments 308 may prevent excessive elongation of the main element 302 and may improve the ability of the element 302 to capture the obstruction.

Referring now to FIGS. 39-42, still another system 400 is shown for removing obstructions from a vascular location. The system includes an obstruction engaging element 402 which works together with a catheter 404 to remove the obstruction. The element 402 is preferably advanced through a lumen 406 in the catheter 404 as described below. The element 402 has an expanding portion 405 which expands to form coils 407 as described herein. The element 402 may be any suitable element 402 which is configured to engage the obstruction such as those described herein.

The catheter 404 has an interlocking structure 410 at the distal end which cooperates with the element 402 to dislodge and remove the obstruction or may be used by itself to engage, dislodge and remove the obstruction. The interlocking structure 410 is preferably a loose, flexible structure formed by flexible filaments 408 such as suture or wire. The filaments 408 are attached to the distal end of the catheter 404 and may form loops 412 or may be woven or interlocked in any manner. The catheter 404 has eight loops 412 attached to the distal end of the catheter 404 with the loops 412 having two different sizes. A radiopaque material 414, such as platinum, may be attached to the filaments 408 at discrete locations to improve radiopacity and to improve the ability of the interlocking structure 410 to become entangled with the element 402 and obstruction. The material 414 may be formed in any suitable manner such as beads of platinum or small coils or tubes attached to the filaments 408.

The relatively flexible nature of the filaments 408 does not substantially increase the stiffness of the catheter 404 so that the catheter 404 can still be advanced through small and tortuous vessels. As the catheter 404 is advanced through the patient's vasculature, the filaments 408 are free to move and displace and will naturally lie against the body of the catheter 404. The catheter 404 may be delivered through another catheter, such as a guide catheter, which is advanced to a location near the obstruction with the catheter 404 being advanced by itself over the guidewire to the obstruction (see FIG. 1). The catheter 404 may even be used by itself to remove an obstruction or may be used with another catheter which encapsulates the obstruction such as the device of FIGS. 43 and 44 described below.

Another method of the present invention is now described with reference to the system of FIGS. 39-42. The guidewire (see FIG. 1) is advanced through the obstruction and the catheter is then advanced through the obstruction over the guidewire. The catheter 404 is then withdrawn a small distance so that the interlocking structure 410 is deployed distal to the obstruction. The guidewire is then withdrawn and replaced by the element 402. The element 402 is then permitted to expand by advancing the element 402 or withdrawing the catheter 404 to expose the element 402. Exposure of the element 402 may cause the element 402 and interlocking structure 410 to naturally become entangled or interlocked. The element 402 may also be twisted or rotated to enhance interaction between the interlocking structure 410 and element 402. The catheter 404 and element 402 are then moved proximally to engage and dislodge the obstruction. Although the entire interlocking structure 410 and expanding portion 405 of the element 402 are shown distal to the obstruction, part of either structure may, of course, be deployed within the obstruction. For example, with reference to FIGS. 40 and 41, the catheter 404 may be advanced into or through the obstruction and then withdrawn into the obstruction so that the loose, flexible filaments 408 are naturally left within the obstruction.

The element 402 is then deployed within the obstruction and the element 402 is manipulated to entangle the element and filaments 408. Of course, some part of the element, such as a few windings of the coil 407, may be deployed distal to the obstruction before withdrawing the catheter 404. After the element 402 and interlocking structure 410 have become entangled, the element 402 is manipulated to dislodge and remove the obstruction.

Referring to FIGS. 43 and 44, still another system 500 for removing an obstruction is shown. The system 500 includes an obstruction engaging element 502 which may be any suitable element such as those described herein. The system 500 also includes a catheter 504 which receives and contains the obstruction during removal from the patient. The catheter 504 has a containment chamber 506 which is defined by a flexible tube 508. The tube 508 may be everted from the position of FIG. 42 to the position of FIG. 43. The tube 508 is made of expanded PTFE but may be made of any other suitable material.

In use, the obstruction engaging element 502 engages the obstruction and the catheter 504 is advanced adjacent to the obstruction as shown in FIG. 43. The catheter 504 and element 502 are then moved proximally together so that the containment chamber 506 everts and covers the obstruction. The catheter 504 and element 502 are then withdrawn from the patient together to remove the obstruction. The flexible containment chamber 506 protects and encases the obstruction to reduce the likelihood of losing pieces of the obstruction as the obstruction is removed.

Referring to FIGS. 45 and 46, still another device 600 for removing an obstruction is shown. The device 600 includes a catheter 602 having a tube 604 mounted to the distal end. The tube 604 has openings 606 therein such as longitudinal slots 608. The device 600 is similar to other devices described herein in that the tube 604 cooperates with an element 610 to dislodge and remove an obstruction. The element 610 is manipulated so that the element 610 extends through one or more of the openings 606 to entangle the element 610 and tube 604. The tube 604 may be deployed distal to the obstruction by advancing the catheter 602 through the obstruction and then withdrawing the catheter 602 to deploy the tube 604. The element 610 is then advanced out of the distal end of the catheter 602 and manipulated to entangle the tube 604 and element 610 together. For example, the element 610 may be twisted and/or pulled proximally. Of course, the element 610 may naturally twist or displace to pass through the openings 606 when advanced from the catheter 602.

While the above is a description of the preferred embodiments of the invention, various alternatives, substitutions and modifications may be made without departing from the scope thereof, which is defined by the following claims. Thus, the preferred embodiments should not be taken as limiting the scope of the invention. For example, although all of the obstruction removal devices described herein are self-expanding structures, the obstruction removal devices may also have actuating mechanisms for moving the engaging element between the expanded and collapsed positions. Furthermore, the present invention is directed to a number of separate inventions and each of these inventions may be claimed independently of one another. Each feature, aspect and advantage of the invention may be claimed independent of one another without departing from the scope of the invention. As a further example, any engaging device, even a balloon, may be used with some of the inventive aspects of the capture element and any capture element may be used with inventive aspects of the engaging device. Finally, the devices of the present invention may also be used in connection with simply controlling blood flow through an area and not necessarily with removal of an obstruction.

What is claimed is:

1. A method of removing an obstruction from a blood vessel, comprising the steps of:
   providing an obstruction removal device having an obstruction engaging portion, the obstruction engaging portion being movable from a collapsed shape to an expanded shape, the obstruction engaging portion being naturally biased toward the expanded shape, the obstruction removal device also having at least one flexible strand which has a proximal end coupled to the obstruction removal device at a proximal location and a distal end coupled to the obstruction removal device at a distal location, the proximal end of the flexible strand being slidably coupled to the obstruction removal device at the proximal location, the flexible strand being connected to a non-expanding portion of the obstruction removal device at the proximal location and the distal location, the obstruction engaging portion being positioned between the proximal and distal locations where the flexible strand is coupled to the obstruction removal device, the obstruction removal device being a single strand extending to a free end;
   advancing the obstruction removal device through a patient's vascular system to the obstruction;
   introducing the obstruction engaging portion into the obstruction with the obstruction removal device in the collapsed shape;
   permitting the obstruction engaging portion of the obstruction removal device to expand within the obstruction after the introducing step;
   manipulating the obstruction removal device so that the obstruction engaging portion and the at least one flexible strand become entangled with the obstruction; and
   removing the obstruction with the obstruction removal device.

2. The method of claim 1, wherein:
   the providing step is carried out with the obstruction engaging portion forming a helical coil.

3. The method of claim 1, wherein:
   the providing step is carried out with the obstruction engaging portion forming a number of coils.

4. The method of claim 1, wherein:
   the providing step is carried out with a plurality of strands slidably coupled to the obstruction removal device.

5. The method of claim 1, wherein:
   the advancing step is carried out by advancing a distal end of the obstruction removal device through the obstruction with the obstruction removal device in the collapsed position; and
   the permitting step is carried out with part of the obstruction removal device expanding distal to the obstruction and part of the obstruction removal device expanding within the obstruction.

* * * * *